United States Patent [19]

Robbins

[11] Patent Number: 4,686,998

[45] Date of Patent: Aug. 18, 1987

[54] PATIENT TEMPERATURE AND HEARTBEAT RATE MONITORING SYSTEM

[75] Inventor: Adam Robbins, San Marcos, Calif.

[73] Assignee: Mediscan Research Limited, Pasadena, Calif.

[21] Appl. No.: 797,164

[22] Filed: Nov. 12, 1985

[51] Int. Cl.$^4$ .............................................. A61B 5/02
[52] U.S. Cl. ................................... 128/670; 128/639; 128/696; 128/736; 128/903
[58] Field of Search ............... 128/639, 670, 903, 736, 128/702, 706; 307/65, 68; 322/9 R, 21, 22, 68

[56] References Cited

U.S. PATENT DOCUMENTS

| | | | |
|---|---|---|---|
| 3,453,546 | 7/1969 | Fryer | 128/903 |
| 3,620,208 | 11/1971 | Higler | 128/638 |
| 3,646,606 | 2/1972 | Buxton et al. | 128/670 |
| 3,851,320 | 11/1974 | Dahl | 128/903 |
| 3,916,877 | 11/1975 | Beckman | 128/670 |
| 4,074,306 | 2/1978 | Kakinama | 128/6 |
| 4,261,370 | 4/1981 | von Nettelhorst | 128/702 |
| 4,270,547 | 7/1981 | Steffen et al. | 128/706 |
| 4,321,933 | 3/1982 | Baessler | 128/903 |
| 4,450,843 | 3/1984 | Barney | 128/670 |
| 4,471,354 | 9/1984 | Smith | 128/903 |
| 4,503,862 | 3/1985 | Baessler | 128/903 |
| 4,521,865 | 6/1985 | Winkler | 364/719 |
| 4,576,178 | 3/1986 | Johnson | 128/670 |

FOREIGN PATENT DOCUMENTS 2913048 10/1980 Fed. Rep. of Germany ...... 128/639

OTHER PUBLICATIONS

"Personal PCM/PDM Biotelemetry System", by Kimmich et al; *Biotelemetry II*, 2nd Int. Symp, May 20-24, 1974, pp. 2-4.

"Biotelemetric Systems", by R. Suzuki, *Jpn. J. Med Electronics & Biol Eng.*, vol. 18, #7, Dec. 1980, pp. 64-70.

*Primary Examiner*—Lee S. Cohen
*Assistant Examiner*—David Shay
*Attorney, Agent, or Firm*—Charles H. Thomas

[57] ABSTRACT

Hospital patient temperatures and heartbeat rates are monitored by providing each patient with a battery powered transmitter containing a reference resistance and to which two sensor electrodes are connected. The first electrode includes a thermistor and is positioned in thermal contact with the patient's skin over the axillary artery. The second electrode is positioned in contact with the patient's skin proximate to the fourth intercostal left parasternal area of the patient's chest. A receiver, carried by a nurse, includes a magnetic actuator for closing a reed switch in a transmitter unit to activate the generation of data signals from that transmitter. The transmitter, when actuated provides an output of modulated, sequential data signals. The data signals are of a duration corresponding to a reference temperature, actual patient temperature, transmitter battery level, and patient heartbeat rate. The receiver includes demodulator circuitry and a microprocessor to provide numerical indicia quantitatively indicative of actual patient temperature and heartbeat rate. The microprocessor compares the demodulated data signals to allowable limits associated with each signal.

12 Claims, 7 Drawing Figures

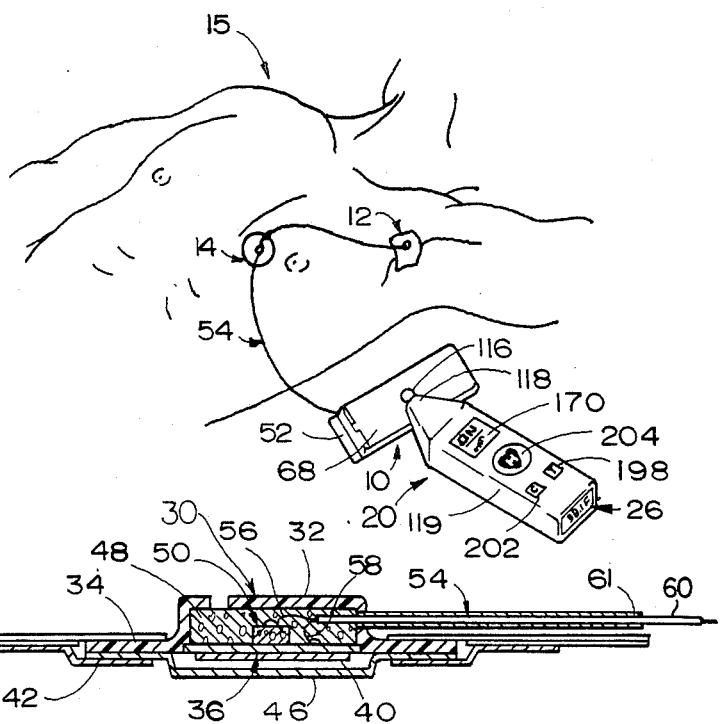
FIG 1
FIG 2
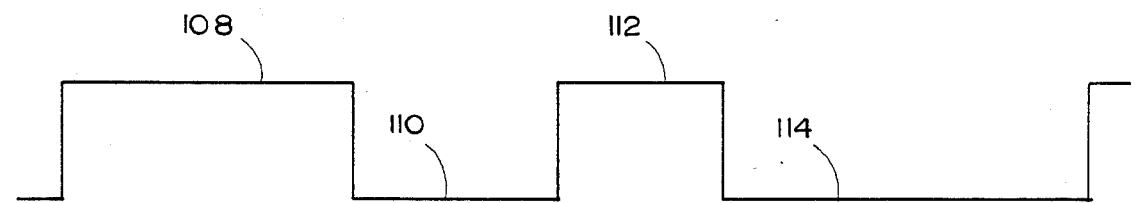
FIG 5
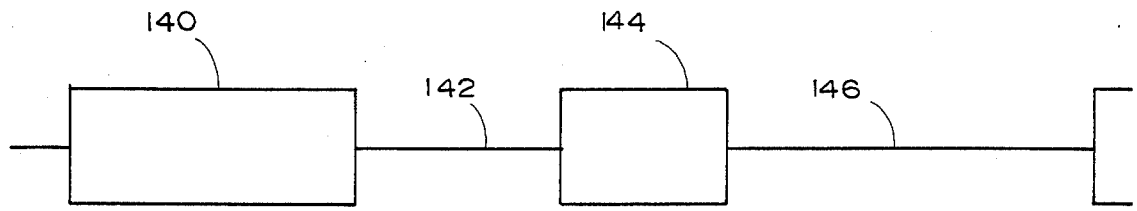
FIG 6

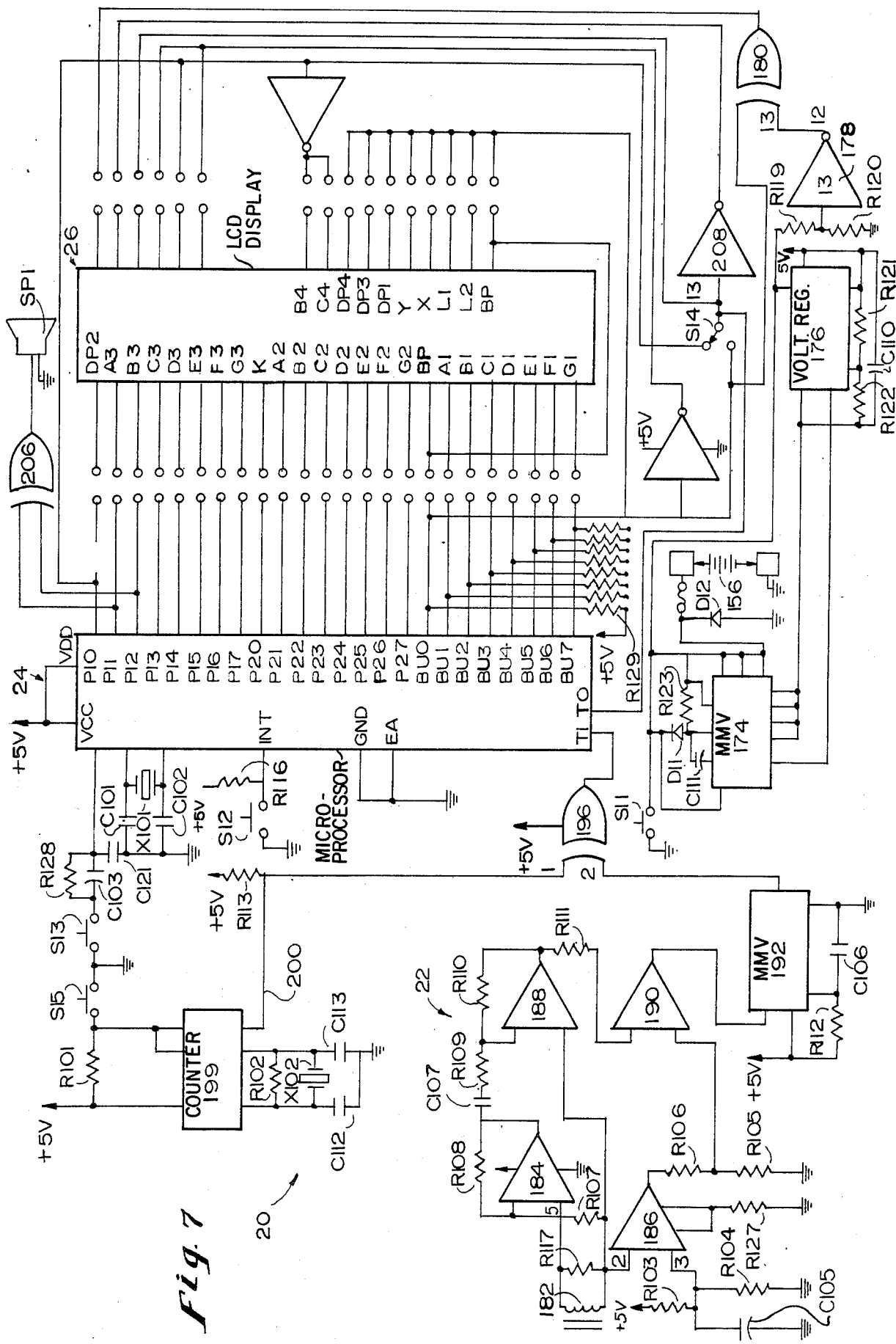

PATIENT TEMPERATURE AND HEARTBEAT RATE MONITORING SYSTEM

BACKGROUND OF THE INVENTION

1. Field Of The Invention

The present invention relates to systems for concurrently monitoring patient temperature and heartbeat rate.

2. Description Of The Prior Art

Various devices have been provided for monitoring temperatures of patients in a hospital using telemetry systems. Prior systems of this type are described in U.S. Pat. No. 3,921,621, U.S. Pat. No. 3,321,933 and U.S. Pat. No. 4,503,862. While prior devices of the type described in the foregoing patents are quite adequate for providing the temperatures of patients in a hospital, it is frequently desireable for the heartbeat rate as well as the temperature of a patient to be monitored. Heretofore, the conventional practice has been for a nurse making rounds to check the pulse rates of patients in a hospital. This is typically performed manually by a registered nurse who stops at the bedside of each patient and holds the patient's wrist to measure the patient's heartbeat rate by taking the patient's pulse rate with a watch. Frequently it is necessary to disturb the patient for this purpose. Also, the task cannot be delegated to less qualified personnel, since the process of manually taking a pulse rate is somewhat subjective and requires accurate judgment. Moreover, since there is a subjective aspect to timing of a pulse rate, nurses must measure the patient's pulse rates for a statistically significant perod of time. Typically, a nurse will manually monitor a patient's pulse rate for sixty seconds. The time required for monitoring is therefore a very significant factor in limiting the number of patients whose pulses can be taken by one nurse making rounds.

Devices do exist for electronically monitoring the heartbeat rates of patients. However, conventional devices for performing this function have been quite complex and normally involve a visual display on the screen of a CRT. Because of the high equipment cost, the use of conventional patient heartbeat rate monitoring devices is normally limited to those patients who are under intensive care. The high cost of purchasing and operating such sophisticated devices is reflected in the high daily charges incurred by a patient in intensive care.

SUMMARY OF THE INVENTION

The present invention is a patient temperature and heartrate monitoring system comprising a plurality of transmitters, one for each patient to be monitored, and a single receiver for monitoring each of the transmitters separately. Each transmitter is comprised of a sensor system for sensing patient temperature and heartbeat rate. Each transmitter also includes a transducer for generating data signals corresponding to patient temperature and heartbeat rate, and a modulator for transforming the data signals to radio frequency signals. The receiver is comprised of a demodulator for sensing the radio frequency signals from a transmitter and for reproducing the data signals therefrom. The receiver also includes a signal processor for producing a visual display from the reproduced data signals.

One object of the present invention is to provide a system for concurrently monitoring patient temperature and heartbeat rate electronically.

Another object of the invention is to provide a patient temperature and heartbeat rate system which employs a number of relatively low cost transmitter units, one for each patient to be monitored, which can be selectively monitored with a single receiver.

A further object of the invention is to provide a means for electronically monitoring patient temperature and heartbeat rate which does not involve disturbing the patient in order to take temperature and heartbeat rate readings. The system employs sensing electrodes which are secured by adhesive to the skin of the patient and which can remain on the body of the patient for up to seven days. The electrodes are connected to the transmitter unit by means of a cable. The transmitter unit is located externally of the patient so that it is accessible for interrogation without disturbing the patient. It is therefore unnecessary to wake a patient who is resting in order to ascertain the temperature and heartbeat rate of the patient.

A further object of the invention is to provide a system for monitoring patient temperature and heartbeat rate which can be automatically interrogated in an instant with a receiver unit without the necessity for a nurse or other hospital attendant to wait while sensors develop electric signals over a sufficient interval to accurately indicate patient temperature and heartbeat rate. To the contrary, the sensors remain present on the skin of the patient and continuously provide passive signals indicative of patient temperature and heartbeat rate. These signals are provided by the sensor elements to the transmitter, but are not transmitted until the transmitter is interrogated by the receiver. Thus, the transmitter does not consume an inordinate amount of power. Nevertheless, the raw signals are developed over a period of time, and are readily available to instantly produce data signals when the transmitter is activated.

Yet a further object of the invention is to provide a patient temperature and heartbeat rate monitoring system which employs sensors of the type familiar to hospital personnel. Moreover, these sensors are positioned on the skin of the patient at positions with which hospital attendants are also quite familiar. One of the sensors is positioned on the skin of the patient over the axillary artery in what is commonly called the apex of the armpit. The other sensor is positioned on the skin of the patient on the patient's chest at an indentifiable point proximate to the fourth intercostal space in the left parasternal area. The sensors are attached to pads containing electrodes of the type commonly employed in electrocardiographic monitoring. The locations at which the electrodes are applied are two of the same locations at which electrodes are applied in electrocardiographic monitoring. Thus, no significant additional training is necessary in order for hospital personnel to properly use the system of the invention.

The invention may be described with greater clarity and particularity by reference to the accompanying drawings.

DESCRIPTION OF THE DRAWINGS

FIG. 1 is a perspective view illustrating one transmitter and the receiver of the invention and the placement of the sensors on the skin of a patient.

FIG. 2 is a sectional elevational detail of a first sensor element employed in the system of FIG. 1.

FIG. 5 is a pulse diagram useful in explaining the generation of data pulses in the transmitter of FIG. 3.

FIG. 6 is a pulse diagram depicting the modulated radio signal output of the transmitter of FIG. 3.

FIG. 7 is a detailed schematic diagram of the receiver of the embodiment of FIG. 1.

DESCRIPTION OF THE EMBODIMENT

Figure 3:
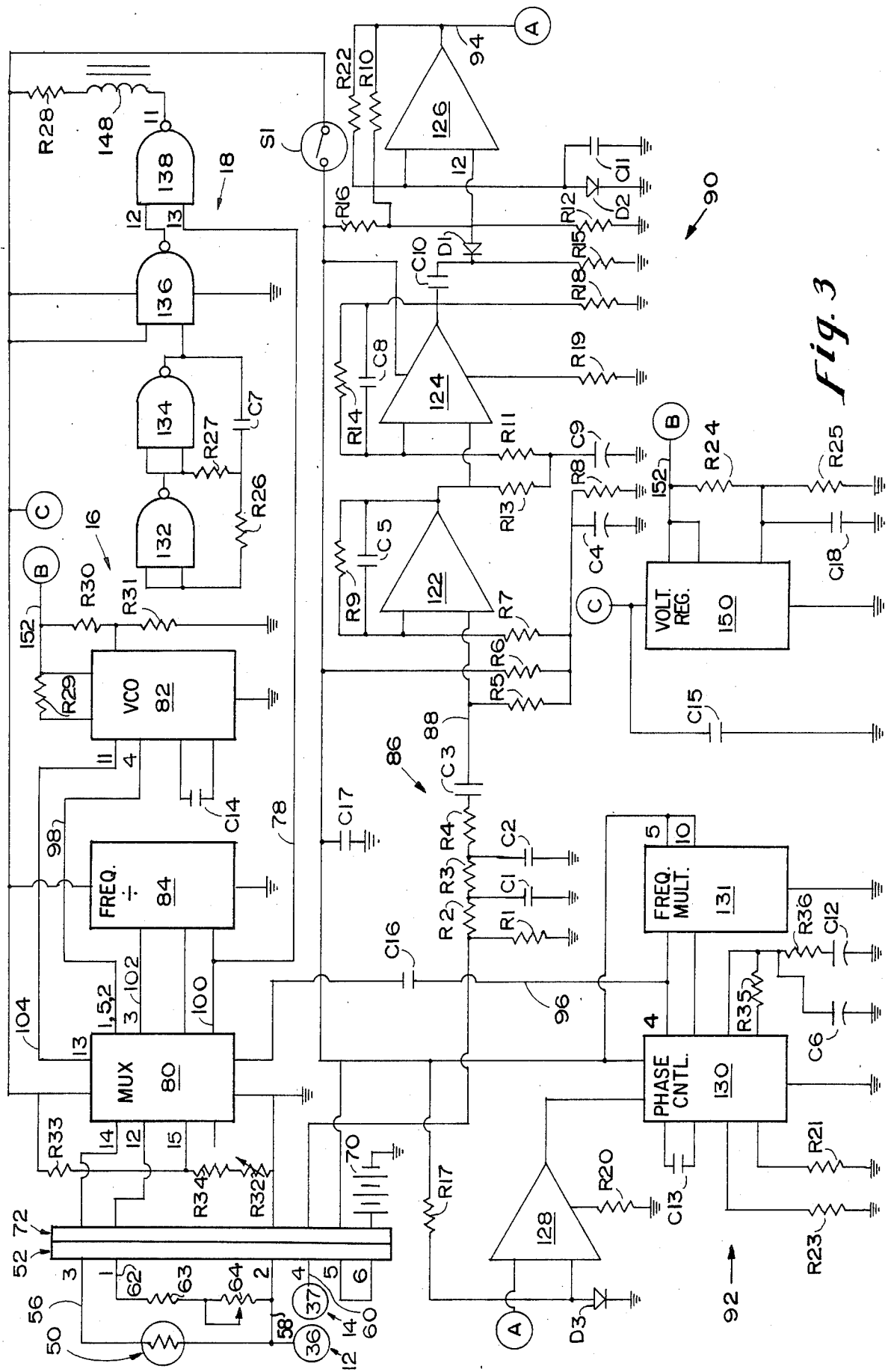
FIG. 3 is a detailed schematic diagram of a transmitter, including sensors, of the embodiment of FIG. 1.

FIG. 1 illustrates a patient temperature and heartbeat rate monitoring system according to the invention. This system is comprised of a plurality of transmitters, one of which is indicated at 10. According to the system, a plurality of transmitters 10 are provided, one for each patient to be monitored. Each transmitter 10 includes first and second sensor elements 12 and 14, respectively. The sensor elements 12 and 14 sense patient temperature and heartbeat rate. The transmitter 10 also includes transducer means, indicated generally at 16 in FIG. 3, for generating data signals corresponding to patient temperature and heartbeat rate. The transmitter 10 also includes modulating means, indicated at 18 in FIG. 3, for transforming the data signals to radio frequency signals. The patient temperature and heartbeat rate monitoring system also includes a receiver 20. The circuit components of the receiver 20 are illustrated in FIG. 7. The receiver 20 includes demodulating mean indicated generally at 22 in FIG. 7, for sensing the radio signals from the transmitter 10 and for reproducing data signals therefrom. The receiver 20 also includes signal processing means, indicated at 24, for producing a visual display from the reproduced data signals on an LCD display 26.

The Sensor Elements

The electrical interconnection of the sensor elements 2 and 14 is depicted in FIG. 3 and the structure of the sensor element 12 is depicted in detail in FIG. 2. Both sensor elements 12 and 14 are similar in construction, although certain differences do exist, as will hereinafter be described.

The sensor elements 12 and 14 both employ plastic, cup-mounted electrodes of the type commonly used for detecting electrocardiographic signals at the surface of the skin of a patient. Both sensor elements 12 and 14 employ a plastic cup housing 30 having a generally raised, disc-shaped center 32 with an axially offset, annular radially extending flange 34. The first sensor element 12 and the second sensor element 14 employ identical first and second disc-shaped electrodes 36 and 37, respectively, each arranged in coplanar fashion with the associated flange 34 so that an adhesive pad 38 extending radially beyond the flange 34 keeps the electrode discs in close contact with the surface of the skin of the patient 15 to which the sensor is affixed. Both of the electrodes 36 and 37 are preferably silver or silver plated and are each initially provided with a gel pad protector 46 which covers a gel pad 40. The gel pad 40 is impregnated with a chemical substance commonly referred to as an electrode gel. The gel pad 40 covers the patient contact surface of each of the electrodes 36 and 37. The gel pad 40 is of the type normally employed with electrodes on electrocardiogram units, and other systems for deriving small electrical signals from the surface of the skin of a patient. The gel pad 40 enhances electrical contact between the surface of the skin of a patient and the electrode discs 36 and 37.

Both of the sensor elements 12 and 14 are initially provided with an annular gel pad protector retainer 42. When the electrode is to be applied to the skin of a patient, the gel pad protector retainer 42 is first removed, and the gel pad protector 46 is then removed. The gel pad 40 is then placed in full contact with the surface of the skin of the patient, and is held in position by the ring of adhesive 44 on the underside of an adhesive pad 38 that overlies the flange 34 of the cup housing 30. An epoxy sealant 48 covers the upper surface of the electrode discs 36 and 37 in both the first sensor element 12 and the second sensor element 14.

In the first sensor element 12 a thermistor 50 in the form of a thermistor die is conductively bonded by means of silver solder to the electrode 36. The sensor elements 12 and 14 are coupled to a sensor interface 52 by a length of cable 54. Within the cable 54 there is a twisted pair of wire conductors 56 and 58. Each of the conductors 56 and 58 is separately sheathed in polyvinylchloride insulation for mutual insulation from the other wire. The conductors 56 and 58 are surrounded by a braided shield 60, indicated in FIG. 3 which is itself insulated by a polyvinylchloride outer cable jacket 61, illustrated in FIG. 2. The conductor 56 is connected to one side of the thermistor 50 by solder. The opposite end of the conductor 56 is connected to a means within the transmitter 16 for applying voltage to it. A separate conductor 62 is connected to one side of a reference temperature resistor pair 63 and 64, as illustrated in FIG. 3. The conductor 58 serves as a ground conductor and is connected to the opposite sides of the reference temperature resistor pair 63 and 64 and the thermistor 50 in an electrical ground through the sensor interface 52.

The braided shield 60 is located within the outer polyvinylchloride cable jacket 61 of the cable 54 and terminates short of the electrode 36, no less than 0.025 inches from the end of the outer jacket 61. The braided shield 60 is thereby electrically isolated from the first electrode 36, but is electrically connected to the second electrode 37 and serves as a heartbeat signal conductor. Together the heartbeat signal conductor 60 and the ground conductor 58 serves as a means for monitoring voltage differential between the first and second electrodes 36 and 37, respectively.

The sensor interface 52 is a combination electronic printed circuit board and edge-type electrical connector or plug. The coupling of the interface 52 has six electrical contacts. Contact 1 is routed to a reference temperature resistor element formed by the pair of reference resistors 63 and 64. Contact 3 of the sensor interface 52 is connected by the wire conductor 56 to one side of the thermistor 50, as previously described, while the ground conductor 58 is soldered directly to the inside surface of electrode 36 adjacent to and in electrical contact with the bonded thermistor die. The ground conductor wire 58 is connected at the sensor interface 52 at contact 2. Contact 4 in the sensor interface 52 is connected to the braided shield 60 of the cable 54. As previously noted, the braided shield 60 is also electrically bonded to the second electrode 37 at a point on the cable 54 between the sensor interface 52 at one end and the first sensor element 12 at the other end. The last two contacts 5 and 6 are connected together by a jumper trace on the circuit board.

The sensor elements 12 and 14 function to sense patient temperature and heartbeat rate. Patient temperature is sensed by the thermistor 50 which is mounted on the first electrode 36 for thermal contact with the skin of the patient 15. The first electrode 36 is secured to the skin of the patient 15 to be monitored in electrical contact therewith. The first electrode 36 and the thermistor 50, together with the reference temperature resisters 63 and 64, form the operative elements of the first sensor element 12. The first electrode 36 in the sensor element 12 is adhesively secured, in the manner previously described, to the skin of the patient 15 in the vicinity of the axillary artery in the apex of the armpit, as depicted in FIG. 1. This location is the clinically specified site for obtaining axillary temperature determinations in humans in conventional hospital practice. The first electrode 36 and the thermistor 50 are affixed so as to obtain and maintain optimum thermal and electrical contact between the first electrode 36 and the skin surface. With the electrode 36 in place, the patient's arterial blood temperature, and hence the skin temperature of the patient in the near vicinity of the axillary artery, are thermally conducted to the thermistor 50.

The thermistor die element forming the thermistor 50 varies in internal resistance to electrical current flow as a linear function of temperature. The variable resistor 64 of the pair of reference resistors 63 and 64 will have been adjusted during manufacture to match the thermistor resistance at a precise, calibrated temperature. Therefore, the exact temperature to which the first electrode 36 and thermistor 50 are exposed can be determined by measuring the difference in resistance between the temperature sensitive thermistor 50 and the fixed series resistance of the resistors 63 and 64.

The patient's heartbeat rate is sensed by affixing the second sensor element 14, including the second electrode 37, to the chest at a point proximate to the fourth intercostal space in the left parasternal area, as depicted in FIG. 1. The pad of the second sensor element 14 is attached to the skin of the patient 15 in the same manner as the pad of the first sensor element 12. As with the sensor element 12, electrode gel is interposed between the surface of the skin of the patient 15 and the contact surface of the second electrode 37 to enhance electrical conduction. With both electrodes 36 and 37 attached to the skin of the patient 15, a voltage will develop across the electrodes 36 and 37. This voltage is proportional to the rate and nature of contraction-relaxation of the heart muscle. The signal provided is commonly known as the electrocardiographic potential and can be detected across numerous sets of points on the body of the patient 15.

The two preferred locations for attachment of the electrodes of the sensor elements 12 and 14 are illustrated in FIG. 1. These locations correspond to the clinically designated unipolar precordial electrocardiographic V2 and 3V6 leads. The sensor elements 12 and 14 are attached to the patient 15 with the sensor element 12 being affixed in the axilla. The sensor element 14 is at approximately the mid-point of the cable 54 and is adhesively attached to the subject's chest. The sensor interface 52 is draped near the top of the patient's garment for convenient attachment to the case of the transmitter 10.

The Transmitter Components

The electrical components of the transmitter 10 are housed in a plastic case 68, depicted in FIG. 1. The electrical components of the transmitter 10 are embodied in two electronic printed circuit boards. The transmitter 10 includes a rechargeable nickel-cadmium 6 volt battery 70 and a socket 72 with contacts aligned for connection to the contacts 1 through 6 of the sensor interface 52. The transmitter case 68 also includes an alligator clip assembly for the purpose of releaseably fastening the transmitter 10 to the garment of the patient 15. The transmitter 10 functions to accept, encode and then telemeter electronic signals which represent the body temperature and heartbeat rate of the patient 15 to which the transmitter 10 and sensor elements 12 and 14 are attached.

The battery 70 provides power through the separate conductors 62 and 56, respectively, to the reference temperature resistors 63 and 64 and to the thermistor 50 for generating a reference temperature signal and an actual temperature signal. The sensor element 12 provides voltage level inputs to contacts 3 and 1 in the sensor interface 52. The voltage level input on contact 1 is proportional to a reference temperature established by the resistors 63 and 64, while the voltage level input on contact 3 is proportional to actual patient temperature as measured by thermistor 50. The sensor elements 12 and 14, respectively, provide inputs to contacts 2 and 4 of the sensor interface 52 at a frequency corresponding to heartbeat rate. Contact 2 is used for a signal ground reference. The transducer 16 is electrically conected to the thermistor 50, the reference resistors 63 and 64 and both of the electrodes 36 and 37.

The transducer 16 generates electrical data signals that include data signals of durations proportional to patient temperature and patient heartbeat rate. These data signals appear on line 78. The signals on line 78 are sequential data signals and are, in sequence: (1) reference temperature data signals of duration proportional to a reference temperature, (2) actual temperature data signals of duration proportional to actual patient temperature, (3) transmitter battery level data signals of duration proportional to transmitter battery level, and (4) heartbeat data signals of a duration proportional to actual patient heartbeat rate. The modulator 18 modulates the electrical data signals on line 78 to provide radio frequency temperature signals and radio frequency patient heartbeat rate signals.

The transducer 16 includes a multiplexer switch 80 coupled to the sensor elements 12 and 14. The transducer 16 also includes a voltage controlled oscillator 82 which is coupled to provide an input to and receive an output from the multiplexer switch 80. The transducer 16 also includes a frequency divider 84 which is connected to receive an input from the voltage controlled oscillator 82 through the multiplexer switch 80 and to provide an output to the multiplexer switch 80. The multiplexer switch 80 receives the voltage level inputs from the sensor elements 12 and 14 and sequentially generates the data signals on line 78.

The transducer circuit 16 also includes a low pass filter circuit 86 coupled to the sensor element 14 for isolating an electrical heartbeat signal having a frequency equal to heartbeat rate. This signal is passed on line 88 to a preamplification circuit 90. The preamplification circuit 90 is coupled between the low pass filter circuit 86 and a phase lock loop circuit 92 and produces an output on line 94 to the phase lock loop circuit 92. The phase lock loop circuit 92 receives the amplified heartbeat signals on line 94 and provides a harmonic heart rate signal to the multiplexer switch 80 on line 96. The harmonic heartbeat signal on line 96 is at a phase controlled frequency which is an upper harmonic of the heartbeat signal on line 94.

Figure 4:
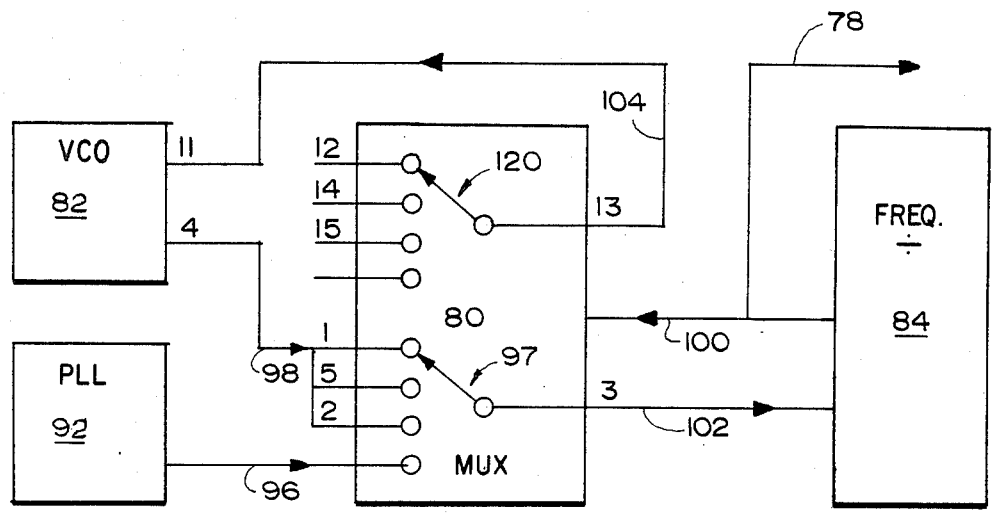
FIG. 4 is a functional diagram useful in explaining the operation of certain of the components of the transmitter of FIG. 3.

The generation of the data signals on line 78 is best illustrated with reference to FIG. 4, which is a functional block diagram of the voltage controlled oscillator 82, the phase lock loop circuit 92, the multiplexer switch 80 and the dividing circuit 84. The multiplexer switch 80 receives inputs from both the phase lock loop circuit 92 and the voltage controlled oscillator 82. The voltage controlled oscillator 82 produces a voltage controlled square wave output signal on line 98 of frequency proportional to input voltage level. Two of the voltage level inputs are provided by the sensor element 12 through pins 1 through 3 of the sensor interface 52. Another voltage level input, proportional to the voltage level of the transmitter battery 70, is provided through pin 15 of the multiplexer switch 80. The voltage controlled square wave output signal on line 98 is provided from the voltage controlled oscillator 82 as an input to the multiplexer switch 80, which in turn provides that signal to the frequency divider 84 on line 102. The frequency divider 84 produces a clock output on line 100 to the multiplexer switch 80. This clock output is proportional to and stepped down from the signal then being supplied as an input to the frequency device 84 on line 102. The clock output on line 100 sequentially gates each of the voltage level inputs through the multiplexer switch 80 to the voltage controlled oscillator 82 on line 104. The clock output from the frequency divider 84 is also connected to the modulating circuit 18 by line 78.

The clock output pulses from the frequency divider 84 serve as the data signals which the modulator 18 modulates with a carrier signal. The phase lock loop circuit 92 is also coupled to the multiplexer switch 80. The low pass filter circuit 86 and the preamplifier circuit 90 are connected to the first and second electrodes 36 and 37, respectively, and monitor the voltage differential between those electrodes to produce heartbeat signals on line 94 responsive to heartbeats of the patient 15. The phase lock loop circuit 92 converts these heartbeat signals to heartrate signals on line 96. The multiplexer switch 80 gates the harmonic heart rate signal on line 96 to the frequency divider 84 in sequence with the voltage controlled square wave output signal from the voltage controlled oscillator 82. Control of the sequencing is functionally equivalent to operation of a wiper switch 97 internally within the multiplexing switch 80. The wipe of the switch is connected to line 102 leading to the frequency divider 84. During the time that the multiplexer switch 80 gates the harmonic heartrate signal from line 96 to the frequency divider 84, the frequency of the clock output from the frequency divider 84 on line 100 is proportional to and stepped down from the harmonic heartrate signal on line 96. These heartrate signals are thereby divided down and form one of the data signals to the modulator 18.

The wave forms of the data signals on line 78 are illustrated in FIG. 5. The first component data signal is a square wave pulse of duration proportional to the reference resistance. This pulse is indicated at 108. The second data signal is of opposite polarity, and is also a square wave signal. This signal is indicated at 110 and is of a duration proportional to the temperature of the patient 15 as measured by the thermistor 50. The third component data signal is a square wave signal 112, which is of a duration proportional to the voltage level of the transmitter battery 70. The fourth and final signal is a square wave pulse 114 which is of a duration proportional to the heartbeat rate of the patient 15. This same sequence of data signal generation is repeated continuously during the time that the transmitter 10 is interrogated by the receiver 20.

The interconnection of the circuit elements and the operation of the circuitry of the transmitter 10 may be described more explicitly with reference to the schematic diagram of FIG. 3. The values of all the resistors and capacitors in both the transmitter 10 and receiver 20 are set forth in Table I at the conclusion of the embodiment description. The transmitter 10 has two modes of operation; quiescent and full power. In the quiescent mode power is supplied to the low pass filter 86, the preamplifier 90, and the phase lock loop circuit 92. In the full power mode the power is applied to all of the circuit elements of the transmitter 10 in FIG. 3 and actual generation of data signals, modulation of data signals, and data transmission occurs.

The voltage level signals from the sensor elements 12 and 14 are received by the transmitter through contacts 1 through 4 of the sensor interface 52. Contacts 4 and 5 of the sensor interface 52 function as a quiescent power mode switch by virtue of the jumper present on the interface 52 between contacts 5 and 6. Thus, connection of the sensor interface 52 to the socket 72 in the transmitter 10 turns on the quiescent power circuit through contacts 4 and 5.

Transition between the quiescent mode and the full power mode is controlled by the operation of a normally open, magnetically operable reed switch S1 in the transmitter. The case 68 of the transmitter 10 is preferably of a dark color with a white target dot at its center, indicated at 116 in FIG. 1. The switch S1 is physically located directly behind the target dot 116 in the case 68. The receiver 20 is equipped with a magnet at the apex 118 of the triangular-shaped end of the receiver case 119. The receiver magnet is a small Cermet disc magnet that is incorporated into one end of the receiving antenna inductor subassembly. The magnet in the receiver 20 serves to close the magnetically operable switch S1 of a transmitter 10 when brought into close proximity thereto. That is, the magnet in the receiver 20 closes the switch S1 when the apex 118 of the receiver case 119 is brought to within one-half inch of the transmitter case target dot 116. Withdrawal of the apex 118 of the receiver 20 to beyond one-half inch of the target dot 116 causes the switch S1 to return to its normally open condition, thereby returning the transmitter 20 to the quiescent mode.

The signals from the sensor elements 12 and 14 are initially processed by the voltage controlled oscillator 82, the multiplexer switch 80 and the frequency divider 84. A low power consumption integrated circuit device commonly designated by the identification number 4046 has a suitable precision voltage controlled oscillator which may serve as the voltage controlled oscillator 82. The voltage controlled oscillator 82 is operated by varying an input voltage in order to obtain an exactly proportional square wave frequency output. In the embodiment depicted in FIG. 3, this output is provided on line 98. An ancilliary controlling parameter is used to select the decade range over which the voltage controlled oscillator 82 is to be operated. This is accomplished by connecting a fixed computed value of resistance between the input pin for this controlling parameter and ground. In the transmitter 10 the voltage divider formed by the resistors R30 and R31 provides a fixed input level to the voltage controlled oscillator 82. The frequency domain adjustment input is then connected to the multiplexer switch 80.

The multiplexer switch 80 is an integrated circuit device commonly identified as a type 4052. Pins 14 and 12 of the multiplexer switch 80 are connected through the sensor interface 52 to the thermistor 50 and the reference resistors 63 and 64, respectively. Pin 15 is an input from a transmitter voltage divider junction formed by resistor R33 on one side and resistors R34 and R32 on the other. As these three connections are sequentially applied to pin 11 of the voltage controlled oscillator 82 the square wave output frequency appearing on pin 4 of the voltage controlled oscillator 82 will change as a direct function of the resistance, or more accurately the current sinking capacity, at each of these three pins. The rate at which the multiplexer switch 80 switches between the inputs on pins 12, 14 and 15 is determined by the voltage controlled oscillator frequency at any given time.

The input to the multiplexer switch 80 from the voltage controlled oscillator 82 is on line 98 to pins 1, 5 and 2 of the multiplexer switch 80. Pin 3 of multiplexe switch 80 is equivalent to a wiper contact of a four pole switch indicated at 97 in FIG. 4. The multiplexer switch 80 sequences from one pole to the next on every transition of the clock input square wave for the frequency multiplexer 80. The clock input to the freqency multiplexer 80 is the output of the voltage controlled oscillator 82 after it has been divided by a factor of 2048 by the frequency divider 84. The frequency divider 84 is commonly identified as a type 4020.

As the multiplexer switch 80 sequences, the dwell time at each position is one-half of the clock square wave cycle. This dwell time is an exact function of the resistance to which the voltage controlled oscillator 82 is then connected. At the fourth switch pole within the multiplexer switch 80 the voltage controlled oscillator 82 is disconnected and replaced by the square wave signal present on line 96 from pin 4 of integrated circuit chip 131 of the phase lock loop circuit 92. The integrated circuit chip 131 may be of a type commonly identified as a type 4046. The output on line 96 represents the ultimate output derived from the low pass filter 86, the preamplifier circuit 90 and the phase lock loop circuit 92, which are the heartrate signal conditioning circuit elements.

The complete output of the multiplexer switch 80 is a composite of the four half square wave cycles or intervals 108–114, depicted in FIG. 5. These intervals comprise a quadrature which contains four separate data values, each encoded as the time duration of the respective interval.

The first interval in the quadrature is the data signal 108, indicated in FIG. 5. The signal 108 represents the reference temperature data from the resistors 63 and 64. The voltage controlled oscillator 82, when connected to these resistances, will oscillate at a fixed reference frequency as determined by the original manufacturing calibration of the reference resistors 63 and 64. This oscillation will be within the range of 9300 to 12,800 hertz. During manufacturing calibration, the sensor 12 thermistor subassembly is immersed in a precision thermal bath which equilabrates the thermistor temperature to 98.6 degrees F. The performance requirement for the thermistor element is that it must exhibit a resistance of 60,700 ohms, +/−5% at this temperature. The reference resistance from the resistors 63 and 64 is then adjusted to match the exact resistance value of the thermistor 50 within its tolerance band. This calibration creates a relation between the thermistor 50 and the reference resistors 63 and 64 that establishes their equality at one precise temperature. Since the thermistor 50 exhibits a known, essentially linear curve in resistance as a function of temperature, application of a fixed algorithm allows computation of the temperature of the thermistor 50 using the measured resistance differential that occurs at temperatures above or below the calibration point.

The second interval in the quadrature of data signals depicted in FIG. 5, is the temperature data signal 110. The voltage controlled oscillator 82, when connected to the sensor thermistor 50, will oscillate in the range of 6,500 to 18,000 hertz which corresponds to a temperature range of from 80.6 degrees F to 120.2 degrees F.

The third data signal in the quadrature is the transmitter battery reference. When pin 15 of the multiplexer switch 80 is internally coupled to the multiplexer switch output line 104, the voltage controlled oscillator input is provided by the voltage divider composed of R33, R34 and R32. The voltage at pin 15 should be between 5.6 and 9.0 volts. The voltage level will determine the amount of current sinking by the voltage controlled oscillator 84 input line, and therefore its frequency. Over the specified range, the voltage controlled oscillator will oscillate at between 3,413 and 20,400 hertz.

The fourth data signal 114 contains the heartrate data and this signal is routed to the multiplexer switch 80 using the heartrate phase lock loop circuit 92 in place of the voltage controlled oscillator 82. The switchover of oscillator sources at this pole of the multiplexer switch 80 is achieved by use of the external pin pole configuration which is possible with the type 4052 IC unit.

The electrocardiographic signal detected by the sensors 12 and 14 through the sensor electrodes 36 and 37 is initially applied to the low pass filter circuit 86. The low pass filter circuit 86 is comprised of resistors R1, R2, R3, R4 and capacitors C1 and C2. The low pass filter 86 attenuates that portion of the heartrate signal above 10 hertz and performs the function of eliminating 60 hertz alternating current power line interferences, as well as other higher frequency potential sources of interference.

The filtered heartbeat signal on line 88 is then routed through the high impedance differential preamplifier circuit 90. The heartrate signal amplification is achieved through four different operational amplifiers 122 through 128, which are each part of a low power consumption integrated circuit, commonly identified as type 4573. The amplified heartbeat signal at the output of amplifier 124 is a negative going pulse with a shape analogous to the electrocardiogram QRS wave. If a pulse of sufficient negative magnitude is applied to the junction of capacitor C10, diode D1 and resistor R15, then enough current will flow through diode D1 to pull non-inverting input on pin 12 of operational amplifier 126 negative. Operational amplifier 126 functions as a comparator and will trigger or produce a square output pulse each time the non-inverting pin 12 thereof goes negative. This results in a relatively uniform heartbeat signal at the output thereof on line 94. Any residual noise or distortion present in the signal at this point is eliminated by passing the signal through operational amplifier 128. Operational amplifier 128 is a clamped comparator stage. The heartbeat signal at the output of operational amplifier 128 should be a uniform, noise-free, fast rise and fall time pulse of approximately four volts amplitude. This pulse appears at a frequency equal to the heartbeat rate.

The phase lock loop circuit 92 includes a 4046 type integrated circuit 130 and a frequency multiplier 4541 type circuit 131. The integrated circuits 130 and 131 operate together to form a phase lock loop circuit. This circuit accepts a repetitive pulse input and produces, by constantly sensing the phase of the input pulse and comparing it to the output, a precisely formed square wave output, the frequency of which is an exact upper harmonic of the input pulse repetition rate. This harmonic heartrate signal is directed to the multiplexer switch 80 on line 96, as previously described.

There are three primary variables which must be adjusted for the proper function of the phase lock loop circuit 92. First, the decade frequency band over which the phase lock loop 92 is to operate must be selected. Selection of the band is achieved by proper selection of resistors R23 and R21, capacitor C13, and selection of the frequency harmonic, or multiple, of the input frequency at which the phase lock loop circuit 92 will operate. Selection of the harmonic frequency is established by setting pins 5 and 10 of integrated circuit 131 at a high level. The settling characteristic of the phase lock loop must also be selected. This characteristic determines the rate at which the phase lock loop output frequency signal on line 96 accomodates any changes in the input frequency. This characteristic is controlled by the filter combination of resistors R35 and R36 and capacitors C6 and C12. The latter characteristic is highly critical, as it effectivly determines the observation time of the heartrate measurement. The particular values of this circuit are set to produce a useable operating frequency band of up to 50 kilohertz. The phase lock loop circuit 92 of the embodiment described provides a frequency multiplication factor of 8192, and a damping factor which provides the equivalent of the heartrate averaged over the preceding 60 seconds. The range of heartrates to be measured is from 20 to 260 beats per minute. Accordingly, the output frequency of the phase lock loop circuit 92 on line 96 will therefore lie within the range from 2,731 hertz to 35,499 hertz.

The output of the phase lock loop circuit 92 from pin 4 of the IC chip 130 is applied to the multiplexer switch 80 on the forth and final pole of the multiplexer switch cycle. As the multiplexer switch 80 cycles from one pole to the next, the frequency of the output of the voltage controlled oscillator 82 or the phase lock loop circuit 92 that is produced by a particular pole position in the multiplexer switch 80 is transmitted as an output to the frequency divider 84 on line 102. The frequency divider 84 divides this signal frequency by 2048 and then returns the signal to the multiplexer switch 80 as a clock signal on line 100. The clock signal steps the multiplexer switch 80 through its pole positions. In this manner, the different frequencies at each pole determine the length of time, divided by 2048 that the switch will dwell at the same pole. The duration of the clock signal from the frequency divider 84 is directly proportional to the voltage levels of the reference resistors 63 and 64, the thermistor 50 and the battery 70, and also to the heartbeat rate derived from the electrodes 36 and 37. The clock signals are also taken from the frequency divider 84 as data signals on line 78 to the modulating circuit 18.

The modulating circuit 18 is an IC chip of quad dual input NAND-gates This chip is commonly sold under the trade designation 4011. The combination of these NAND-gates, the resistors R26 and R27 and the capacitor C7 form a square wave oscillator which is set to operate at approximately 50 kilohertz. The four NAND-gates are depicted at 132, 134, 136 and 138 in FIG. 3. NAND-gate 136 serves as a buffer for the carrier frequency signal which is applied to the pin 12 input of the NAND-gate 138. The data signals of FIG. 5 are applied to the other input pin 13 of NAND-gate 138. The data input signals of FIG. 5 modulate the 50 kilohertz carrier output on pin 11 of NAND-gate 138.

The modulated carrier signal is comprised of signal bursts separated by time intervals. The signal bursts 140 and 144 of the radio frequency output of the modulating circuit 18 are depicted in FIG. 6. The signal bursts 140 and 144 correspond, respectively to the data signals 108 and 112 of FIG. 5. The intervals between signal bursts, indicated at 142 and 146, correspond respectively to the data signals 110 and 114 of FIG. 5. The modulated carrier signal of FIG. 6 is applied to the antenna inductor 148 and the current limiting resistor R28 in the transmitter 10.

The transmitter 10 also employs a special voltage regulator integrated circuit indicated at 150 in FIG. 3 and commonly identified in the trade as type 7663. The voltage regulator chip 150 is employed to precisely control the power supply voltage provided to the voltage controlled oscillator on line 152. The unique manner in which the voltage controlled oscillator 82 is configured as a resistance sensing voltage controlled oscillator requires that the supply voltage thereto must be regulated at a fixed level and isolated from the other circuit elements.

The Receiver

The receiver unit 20 is depicted schematically in FIG. 7. The receiver unit 20 consists of four printed circuit boards, a liquid crystal display (LCD) 26, a rubber key pad employing conductive rubber contacts, and a battery 156 all housed within an impact resistant plastic case 119, depicted in FIG. 1. The battery 156 is accessible through a removeable battery compartment door on the underside of the housing 119. The four printed circuit boards include one switch pad trace board for use with the conductive rubber key pad, one connector trace board for connection of signals to the LCD unit, and two electronic printed circuit boards which contain the receiver circuitry.

The receiver 20 functions to first activate transmission of signals from the transmitter unit 10, receive and condition those signals, then reproduce and pass the data signals to the receiver microprocessor 24. The microprocessor 24 performs data validity checks and data reduction, including scaling, compensation, and final computation. The microprocessor 24 then presents numeric data signals to the LCD display 26. The receiver 20 also monitors the level of its own battery 156 and detects transmitter low battery warnings.

Receiver power is turned on by momentarily depressing the "ON" touch pad 170 illustrated in FIG. 1. The touch pad 170 operates the switch S11. The switch S11 activates a large time constant RC oscillator, which is comprised of capacitor C111, resistor R123 and a dual monostable multivibrator 174. The monostable multivibrator is an integrated circuit commonly identified in the trade as a type 4538. The monostable multivibrator 174 is triggered into the "on" state as a one shot multivibrator by the "ON" touch pad contact 170. In the "on" state, the multivibrator 174 provides battery power to voltage regulator 176. The voltage regulator 176 is an integrated circuit commonly identified in the trade as a type 7663 IC. The voltage regulator 76 is controlled by the values of resistors R122, R121 and capacitor C110 to provide regulated +5 volt direct current power to the other receiver circuit elements for as long as the multivibrator 174 remains in the "on" state. If the "ON" contact 170 is made and released, the multivibrator 174 will return to the "off" state after the elapse of 30 seconds. If pressure is maintained on the "ON" contact pad 170, the switch S11 is held closed and the multivibrator 174 will remain in the "on" state indefinitely.

An inverter element 178 is used to monitor the regulated +5 volt direct current power level. The inverter 178 is one of six inverter elements on an integrated circuit commonly identified in the trade as a type 4069 hex inverter IC. Pin 13 input of the inverter 178 receives an input from a voltage dividing circuit formed by resistors R119 and R120. When the voltage level at pin 13 falls below 1 volt, the output of the inverter at pin 12 switces from a low to a high logic level. This changes the input state of pin 13 of an exclusive OR-gate 180. The OR-gate 180 may be one of four exclusive OR-gates in a chip commonly identified in the trade as a quad, dual input exclusive OR-gate IC type 4070.

Normally, the output of exclusive OR-gate 180 suppresses display of the LCD "Lo Bat" signal by shorting that display element to the baseplate of the LCD 26. A high logic level on pin 13 of exclusive OR-gate 180, however, will turn off the gate and allow the "Lo Bat" element to be strobed by the 60 hertz LCD display signal provided by the microprocessor 24.

The demodulation circuitry 22 of the receiver 11 demodulates the patient temperature signals and the patient pulse rate signals, indicated at 140–146 in FIG. 6 from the transmitter 10. The demodulating circuitry 22 provides envelope signals of duration proportional to the electrical data signals 108–114, depicted in FIG. 5.

As previously indicated, positioning of the apex 118 of the case 119 of the transmitter 20 proximate to the target disc 116 of the transmitter 10 closes the switch S1 in the transmitter 10. This activates the transmitter 10 to produce a radiated transmission of a 50 kilohertz data modulated carrier signal, as depicted in FIG. 6. This signal is sensed by the inductor antenna 182 in the receiver 20. The detected radio signal is applied across resistor R117 and to pin 5 of preamplifier stage 184 on one side of the resistor R117. The signal is also applied to pin 2 of amplifier 186 on the other side of the resistor R117. Amplifiers 184, 186, 188 and 190 are amplifier stages of a quad operational amplifier commonly identified in the trade as a type 4573 IC.

A voltage dividing network is provided and is composed of resistors R103, R104 and capacitor C105. A tap from this voltage dividing network is coupled to the second input, pin 3 of amplifier stage 186. The output of amplifier stage 186 provides a voltage reference to amplifier stages 184 and 188.

The modulated high frequency signal detected by inductor antenna 182 is amplified by the network made up of amplifier stages 184 and 188, resistors R107, R108, R109 and R110, and capacitor C107. The gain of this network is approximately 300. Resistors R106 and R105 make up a voltage divider which delivers a voltage 0.03 volts DC below the reference output of amplifier stage 186. The voltage tap between resistors R105 and R106 and the output of amplifier stage 188 are applied, respectively, to the two inputs of amplifier stage 190, thus causing the amplifier stage 190 to function as a level detector. When the output of amplifier stage 188 exceeds the voltage level between resistors R105 and R106, the output of amplifier stage 190 changes state. This produces a clean replication or reproduction of the modulated 50 kilohertz data signal depicted in FIG. 6.

The output of amplifier stage 190 is coupled to a demodulating element 192. The demodulating element 192 is one-half of a chip commonly identified as a dual monostable multivibrator IC, type 4538. The demodulating element 192 demodulates the transmitted data signal. When the multivibrator 192 receives an input trigger signal from amplifier stage 190, the network of resistor 112 and capacitor 106 acts to control the duration of the output of the multivibrator 192. Resistor 112 and capacitor 106 establish the duration of the output pulses of the multivibrator 192 at 50 microseconds. If multivibrator 192 is retriggered within this 50 microsecond interval by another input pulse, the output of multivibrator 192 will be extended in duration accordingly. Since the carrier frequency of the transmitter 10 is set at approximatly 50 kilohertz, the single pulse duration for carrier pulses will be 10 microseconds. Therefore, as long as carrier pulses are present at the input of multivibrator 192, this multivibrator will remain turned "on". Multivibrator 192 thereby produces a demodulated pulse train output which is a reproduction of the data signals on line 78 before they are modulated by the modulating circuit 18 in the transmitter 10.

The output of the demodulator 192 is provided to the T1 input of microprocessor 24. The microprocessor 24 may be one of several microprocessors, among which are the types 8049, 80C49, 80H49. Other equivalent models may be employed as the microprocessor 24. The output of the demodulator 192 is transmitted to the T1 input of the microprocessor 24 through pin 2 of the exclusive OR-gate 196. Piezoelectric speaker SP1 and its exclusive OR-gate driver 206 are used by the microprocessor 24 as an enunciater to signal the user that valid data has been received.

As long as the second input on pin 1 to the exclusive OR-gate 196 remains high, the output of the exclusive OR-gate 196 will pass to the microprocessor 24. The input to pin 1 of exclusive OR-gate 196 remains high unless the test button 198 in FIG. 1 is depressed. Test button 198 operates switch S15 in FIG. 7. When switch S15 is closed, a 14 stage ripple carry binary counter 199 is activated. One suitable ripple counter 199 is available as a type 4060 IC. The network of resistor R102, crystal X102 and capacitors C112 and C113 combine with input elements within the ripple counter 199 to form a 1.0 MHz square wave oscillator. This signal is counted down in the binary counter chain by a factor of 16384 to provide an output signal on line 200 of 61.035 hertz. This signal is formed of square wave pulses of 8.192 miliseconds duration, +/−0.5%. This precision test signal appears on pin 1 of exclusive OR-gate 196. The exclusive OR-gate 196 thereupon applies the signal from line 200 to the T1 input of the microprocessor 24.

The microprocessor 24 directly utilizes several networks and associated components in normal operation. One network is composed of a crystal X101 and capacitors C101 and C102 to provide the microprocessor 24 with a 6 MHz square wave clock signal. Another network is formed of switch S13, resistor R128 and capacitors C103 and C121 to provide the proper "Clear" or reset ground signal to the microprocessor 24 when switch S13 is activated. Switch S13 is activated by depression of the button 202 on the receiver case 168. The "clear" signal stops any current microprocessor program function and returns the microprocessor 24 to an initial readiness state.

The combination of switch S12 and resistor R116 provide the microprocessor 24 with a mode switching ground signal when the switch S12 is depressed. Switch S12 is operated manually by depression of the button 204 on the receiver case 168. Operation of the switch S12 commands the microprocessor program to toggle between the two functional display modes of which the microprocessor 24 is capable. That is, switch S12 toggles a display as between patient temperature and patient heartrate in the LCD display 26.

Resistor R129 is a resistor network device which provides a +5 volt DC pull-up level to the BU buss lines on microprocessor 24. The resistor network R129 maintains the LCD display 26 in an "off" state when the display elements are not in use.

The liquid crystal display LCD 26 is the final adjunct to the microprocessor 24. The display 26 is a 0.3 inch high, 3 and ½ digit LCD display with one decimal point and a "Lo Bat" unitary message. The display 26 is driven by a 60 hertz baseplate signal provided by microprocessor 24. The elements in the LCD display 26 to be displayed are toggled by the same baseplate signal in phase. Those elements which are to remain blank are toggled by the signal 180 degrees out of phase.

The centigrade/fahrenheit display mode is determined by the setting of switch S14, operated by button 202 on the receiver case 168. The switch S14 controls the state of the inverter element 208 and the T0 input to microprocessor 24. The action on inverter 208 determines whether elements of the right-most digit/letter will display as an "F" or a "C". The T0 state determines which temperature convention algerithm will be applied by the microprocessor 24 during numerical computations.

The performance of the receiver 20 is controlled by a unique computer program which resides in the memory of the microprocessor 24. The listing of such a program is attached hereto as Appendix A, as implemented in an 8049 type microprocessor with 128 bytes of RAM and 2 kilobytes of program memory. Data signals applied to the microprocessor 24 consist of two complete variable pulse width square wave cycles. One of these positive/negative cycles represents the temperature data while the other positive/negative cycle represents transmitter battery reference and heart rate data. These cycles are reproductions of the data signals 108–114 depicted in FIG. 5.

In the first cycle, the duration of the initial positive going interval or pulse corresponds to the temperature reference controlled frequency. The duration of the negative going half of the cycle represents the thermistor controlled frequency. In the second cycle, the duration of the first positive going pulse is a function of transmitter battery level. The duration of the negative going half of the second cycle corresponds to the frequency of the transmitter heart rate monitor.

In the ready state, the microprocessor program monitors the input line T1 for a positive going pulse in the 80 to 110 milisecond duration range. This is the acceptable range for the temperature reference data signal 108, depicted in FIG. 5. If such a signal is detected, the processor proceeds to read the next sequential two complete cycles. When this quadrature of data has been received and stored, it is checked for valid intervals and characteristics. Any errors are flagged and the display for either of the two categories of data (temperature and heart rate) which contain the errors will signal the deficiency with an "Err" message display in the LCD display 26. If the data stream is interrupted in the midst of reception, the microprocessor 24 will wait one second for renewed reception. After one second has elapsed, an "Err" message will be displayed indicating a transmission fault. If acceptable data is received intact, the microprocessor 24 will sound a one second audible tone via the enunciater SP1 indicating to the operator that transmission is complete.

The actual data received and stored by the processor is in the form of clock unit counts. These represent numerical values of microprocessor clock frequency pulses that equal the duration of the input data pulses. All data computations and manipulations are done with the data in this numerical form. Conversion to discrete standard units, such as degrees, is performed just prior to display of the data.

The first step in processing temperature data is to apply correction factors based on known thermistor response deviation. After this compensation, the generalized equation for final temperture (FTEMP) calculation using Reference Count (CR) and Temperature Count (CT) data is:

$$FTEMP = 98.6((CR-CT)/(CR+CT))*90$$

Since integer arithmetic is employed, the above equation is transformed to:

$$20*FTEMP = 1972 + 1800*CR/(CR+CT) - 1800*CT/(CR+CT)$$

After FTEMP is calculated a value, TFLAG, is checked. If TFLAG is within a set range an additional compensation is computed. Then, the Compensated Final Temperature (CFTEMP) is calculated by:

$$CFTEMP = 1.0645*(FTEMP - 6.3607) \ [decimal]$$

The actual algorithm used by the microprocessor 24 is:

$$20*CFTEMP = 1.0645*([20*FTEMP] - 127.214) \ [decimal]$$

This experimentally derived correction accounts for non-linearity which occurs in certain ranges of transmitter voltage controlled oscillator operation. Accuracy is preserved in these computations by utilizing a four decimal place fixed point format and dividing by 10,000 [decimal] at the end of a calculation. All calculations are performed in binary and converted to binary coded decimal after computation and division of the result by 2 to give FTEMP in tenths of a degree.

The first positive pulse of the second cycle is read into memory and then compared against program values. A pulse width equalling 199 milliseconds or less creates a low transmitter battery error flag. This results in a "rb-" warning display and invalid data state.

The negative pulse of the second cycle is read into memory as Heart rate count (CHR). The final heart rate data is expressed in beats per minute (BHR). Heart rate is calculated as follows:

$$BHR = (60*1.031746032)/CHR*15.1*4*2$$
$$= 512457/CHR \text{ [decimal] or}$$
$$= 07D1C9/CHR \text{ [hexadecimal]}$$

Since the heart rate data frequency is effectively multiplied by 4 in the transmitter 10, the time interval corresponding to the half cycle which is actually transmitted and counted is decreased by the factor 4*2=8. The value of 15.1 microseconds represents the normalized count time while the initial decimal correction number is a experimentally derived compensation factor.

If the microprocessor 24 detects an input signal between 8.147 and 8.238 milliseconds it is accepted and identified as a test signal. If all functions are operating correctly, the microprocessor 24 will display the normal numerical displays of 98.6 degrees F. on 37.0 degrees C. or 60 H (for 60 beats per minute heart rate). Any other response to a test signal indicates a failure mode within the receiver.

Undoubtedly, numerous variations and modifications of the invention will become readily familiar to those with patient temperature and heartbeat rate monitoring devices. Accordingly, the scope of the invention should not be construed as limited to the specific embodiment of the invention depicted and described, but rather is defined in the claims appended hereto.

TABLE I

| Capacitors (microfarads, unless otherwise noted) | | | | |
|---|---|---|---|---|
| C1,C2 | .002 | | C101,C102 | 20 pf |
| C3 | .1 | | C103 | 1.0 |
| C4 | 1.0 | | C105 | 2.2 |
| C5 | 1000 | pf | C106 | 220 pf |
| C6 | 10 | | C107 | 22 pf |
| C7 | 100 | pf | C109 | .47 |
| C8 | 1000 | pf | C110 | 22 |
| C9 | 1.0 | | C111 | 10 |
| C10 | .1 | | C112 | 22 pf |
| C11 | .1 | | C113 | 22 pf |
| C12 | 47 | | C121 | .1 |
| C13 | 100 | pf | | |
| C14 | 1000 | pf | | |
| C15 | .05 | | | |
| C16 | 1000 | pf | | |
| C17 | 10 | | | |
| C18 | .1 | | | |

| Resistors (ohms) | | | | | | | |
|---|---|---|---|---|---|---|---|
| R1 | 470 K | R19 | 2.2 M | R101 | 100 K | R122 | 390 K |
| R2 | 2.2 M | R20 | 2.2 M | R102 | 1.0 M | R123 | 2.7 M |
| R3 | 2.2 M | R21 | Selected | R103 | 6.8 V | R124 | 100 K |
| R4 | 2.2 M | R22 | 2.2 M | R104 | 22 K | R127 | 100 K |
| R5 | 2.2 M | R23 | 270 K | R105 | 100 K | R128 | 100 K |
| R6 | 1 M | R24 | 1.2 M | R106 | 10 K | R129 | 47 Kx8 |
| R7 | 100 K | R25 | 560 K | R107 | 10 K | | |
| R8 | 1.0 M | R26 | 22 K | R108 | 200 K | | |
| R9 | 20 M | R27 | 82 K | R109 | 20 K | | |
| R10 | 2.2 M | R28 | 1.0 K | R110 | 300 K | | |
| R11 | 100 K | R29 | Selected | R111 | 22 K | | |
| R12 | 300 K | R30 | 100 K | R112 | 110 K | | |
| R13 | 1.0 M | R31 | 300 K | R113 | 1.0 M | | |
| R14 | 10 M | R32 | 50 K | R116 | 2.7 M | | |
| R15 | 10 M | R33 | 680 K | R117 | 2.7 K | | |
| R16 | 20 M | R34 | 82 K | R119 | 680 K | | |
| R17 | 1.0 M | R35 | 1.8 M | R120 | 470 K | | |
| R18 | 1.0 M | R36 | 180 K | R121 | 1.1 M | | |

APPENDIX A

```
; MODIFIED FOR VOLTAGE TO FREQUENCY CONVERTER CONFIGURATION
;
;TRANSMITTING CLINICAL THERMOMETER, TOGETHER WITH
;TRANSMITTING HEART RATE MONITOR.
;
;       THIS PROGRAM ASSUMES IMPLEMENTATION OF AN 8049
;MICROPROCESSOR WITH 128 BYTES OF RAM AND 2K BYTES PRO-
;GRAM MEMORY.
;
;TRANSMISSION FROM REMOTE UNIT CONSISTS OF 2 BURST-NOBURST
;CYCLES. ONE BURST-NOBURST CYCLE REPRESENTS THE TEMPERATURE
;DATA, AND THE OTHER CYCLE CONSISTS OF THE REFERENCE BURST
;AND THE RR INTERVAL NOBURST.
;
;IN THE TEMPERATURE MAJOR PHASE, THE BURST SUBPHASE CORRESPONDS
;TO THERMAL REFERENCE OSCILLATOR TRANSMISSION, AND THE NOBURST
;SUBPHASE TO THE THERMAL DATA OSCILLATOR TRANSMISSION.
;       TEMPERATURE IS COMPUTED ON THE BASIS OF DUTY CYCLE
;OF THE TEMPERATURE MAJOR PHASE.
;
;       THE NOBURST SUBPHASE DURATION REPRESENTS THE RR INTERVAL
;DIVIDED BY 4. THE RR (NOBURST) SUBPHASE DURATION WILL RANGE
;FROM 62.5MS TO 625MS, CORRESPONDING TO A HEARTRATE OF 240 TO
;24 BPM. TO COMPUTE HEARTRATE IN BPM--
;       HR=(60SEC/MIN)/COUNT*15.1uS*4*2 (NOTE...EXPERIMENTAL
;TEST PROCEDURES ON A RANDOM SAMPLING OF COMPLETED TRANSMITTERS
;LED TO THE INSERTION OF A CORRECTION CONSTANT INTO THE ABOVE EQUATION
;TO COMPENSATE FOR A HARDWARE INDUCED LINEARITY ERROR)
;(THE HEARTRATE FREQUENCY IS MULTIPLIED BY 4 IN THE TRANSMITTER)
;
;TO ACCOMODATE THE TEMPERATURE ONLY VERSION, THE PROGRAM
;LOOKS FOR A BURST SUBPHASE OF DURATION 80-110MS (CORRESPONDING
;EQUATES ARE LSMIN,MSMIN,LSMAX,MSMAX-VALID DATA WINDOW) AND
;UPON RECEIVING THAT BURST SUBPHASE, PROCEDES TO READ 2 FULL
;BURST NOBURST CYCLES. IN THE FULL VERSION, ONE WILL
```

```
;REPRESENT THE TEMP MAJOR PHASE AND ONE THE RR MAJOR PHASE.
;       THE RECEIVED QUADRATURE IS THEN CHECKED FOR VALID
;INTERVALS AND ERROR CHARACTERISTICS ARE FLAGGED. ERRORS IN
;EITHER THE TEMPERATURE DATA OR THE HEARTRATE DATA WILL BE
;INDICATED WHEN THE INSTRUMENT IS IN THOSE RESPECTIVE MODES.
;
;IF, WHILE RECORDING THE 2 MAJOR BURST-NOBURST CYCLES, THE
;PROBE IS WITHDRAWN AND NO MORE DATA IS PROVIDED, A ONE SECOND
;TIMER WILL LAPSE AND THE DISPLAY WILL INDICATE A READ ERROR
;CONDITION. IF AN ERROR CONDITION OCCURS AFTER AN INPUT SIGNAL
;IS DETECTED BUT BEFORE THE MAJOR CYCLE RECORDING STARTS THEN
;THE PRE-READ STATUS IS RESTORED. UPON COMPLETION OF THE DATA
;TRANSFER FROM TRANSMITTER TO RECEIVER THE RECEIVER UNIT WILL
;"BEEP"(DISCRETE CONFIGURATION ONLY), INDICATING TO THE
;OPERATOR THAT THE TRANSMISSION IS COMPLETE.
;*************************************************************
;
;           *** UTILITY SUBROUTINES PROVIDED ***
;
;A NUMBER OF UTILITY SUBROUTINES ARE PROVIDED;
;
;ERRR
;           ROUTINE PRINTS 'Enn', WHERE nn IS THE ACCUMULATOR
;           CONTENTS. USED TO INDICATE TO OPERATOR THE NATURE
;           OF AN ERROR CONDITION.
;
;CLEAR
;           CLEAR LOCATIONS 20-27.
;MOVE
;           MOVE BYTE POINTED TO BY R0 TO WHERE R1 POINTS, AND
;           INCREMENT BOTH POINTERS.
;MOVE2
;           MOVE 2 BYTES FROM @R0 TO @R1
;MOVE4
;           MOVE 4 BYTES FROM @R0 TO @R1
;DISPLY
;           COMPLEMENT THE DISPLAY REGISTER CONTENTS AND RESTART
;           THE TIMER. CONTROLS PHASE REVERSING OF LCD.
;BINBCD
;           CONVERT THE TWO BYTE BINARY VALUE STORED IN 20-21 TO A
;           PACKED BCD NUMBER IN 3A-3C.
;SUBBIN
;           SUBTRACT THE FOUR BYTE UNSIGNED BINARY NUMBER IN
;           24-27 FROM THE 4 BYTE NUMBER IN 20-23. LEAVE
;           RESULT IN 20-23. RETURN CARRY BIT SET IF THE LATTER
;           IS SMALLER.
;           R0,R1, AND R2 ARE PRESERVED IN THIS ROUTINE.
;ADDBIN
;           ADD THE FOUR BYTE UNSIGNED BINARY NUMBER IN 20-23
;           TO THE NUMBER IN 24-27. RESULT IN 20-23. R0, R1,
;           AND R2 ARE PRESERVED.
;MLTBIN
;           MULTIPLY THE FOUR BYTE BINARY NUMBER IN 20-23
;           BY THE TWO BYTE BINARY NUMBER IN 26-27. RESULT
;           IN 20-25. USES LOC(24-25).
;DIVBIN
;           DIVIDE THE FOUR BYTE BINARY NUMBER IN 20-23 BY
;           THE TWO BYTE BINARY NUMBER IN 26-27. RESULT IN
;           LOC 28-2B. USES LOC(24-25).
;SHIFTL
;           SHIFT THE CONTENTS OF LOCATION POINTED TO BY R0
;           THROUGH R0+R2 LEFT ONE BIT. INCLUDES CARRY IN,
;           CARRY OUT.
;SHIFTR
;           SHIFT THE CONTENTS OF LOCATION POINTED TO BY R0
;           THROUGH R0+R2 RIGHT ONE BIT. INCLUDES CARRY IN,
;           CARRY-OUT.
;LIMIT
;           TEST LIMITS OF 2 BYTES @ TESTVAL. COMPARES TO
;           2 BYTES AT LIMMIN AND 2 BYTES AT LIMMAX.
;           @LIMMIN < @TSTVAL <@LIMMAX  YEILDS NO CARRY
```

```
;       @LIMMIN > @TSTVAL   YEILDS CARRY AND RETURNS ACC=F0H
;       @LIMMAX < @TSTVAL   YEILDS CARRY AND RETURNS ACC=F1H
;*************************************************************
;              ***   RAM MEMORY MAP   ***
;
; 00 GENERAL REGISTER 0 - DATA COUNTER 0
; 01                   1   DATA COUNTER 1
; 02                   2
; 03                   3
; 04                   4
; 05                   5
; 06                   6
; 07                   7
; 08 TOP OF STACK
;  -
; 17 BOTTOM OF STACK
; 18 ALTERNATE GENERAL REGISTER 0 - ALTERNATE DATA COUNTER 0
; 19     !                       1 - ALTERNATE DATA COUNTER 1
; 1A     !                       2
; 1B     !                       3
; 1C     !                       4
; 1D     !                       5
; 1E     !                       6
; 1F ALTERNATE GENERAL REGISTER 7
; 20    (BEGINNING OF SCRATCHPAD MEMORY)
;  -               !
; 27    (END OF SCRATCHPAD MEMORY)
; 28-31 (INTERMEDIATE STORAGE AND RESULT OF DIVBIN)
; 32 FIRST BURST SUBPHASE LESS SIGNIFICANT PART
; 33 FIRST BURST SUBPHASE MORE SIGNIFICANT PART
; 34 FIRST NOBURST SUBPHASE LESS SIGNIFICANT PART
; 35 FIRST NOBURST SUBPHASE MORE SIGNIFICANT PART
; 36 SECOND BURST LESS SIGNIFICANT PART
; 37 SECOND BURST MORE SIGNIFICANT PART
; 38 SECOND NOBURST LESS SIGNIFICANT PART
; 39 SECOND NOBURST MORE SIGNIFICANT PART
; 3A BINBCD DESTINATION LSP
; 3B BINBCD DESTINATION NLSP
; 3C BINBCD DESTINATION MSP
; 3D DISPLAY BUFFER BYTE 1: LS BIT IS DEC PT
; 3E DISPLAY BUFFER BYTE 2: LS BIT IS MOST SIGNIF. "1"
; 3F DISPLAY BUFFER BYTE 3: LS BIT IS BP CON
; 40 TREF COUNT
; 42 TDAT COUNT
; 44 REF PULSE
; 46 RR COUNT
; 48 INTERMEDIATE STORAGE DATA LOCATION
;  -
; 57 END INTERMEDIATE STORAGE AREA
; 58-59 FAHRENHEIT TEMPERATURE (BINARY)
; 5A-5B CENTIGRADE TEMPERATURE (BINARY)
; 5C-5D HEARTRATE (BINARY)
; 60 CFGFLG    ;USES MS 2 BITS. NORM=1X,CFG1=01,CFG2=00
; 61 HRFLG    ;HEARTRATE OR TEMP FLAG. 00=TEMP, FF=HEARTRTE
; 62 THMERF   ;THERMTIME ERR FLG 00HL 00HL (REF=HI NIB,DAT=LO)
; 63 FCFLG    ;FAHRENHEIT=00, CENTIGRADE=FFH
; 64 RRERF    ;RR TIM ERROR FLAG  00HL 00HL( THESE 0 IF OK)
; 65 TSTFLG
; 66 EXTINT
; 67 LBERF
; 68 TFLG     ;FLAG SET IF TEMP IS GREATER THAN 98.6 F
; 70-76       ;ALTERNATE STACK STORAGE AREA
;*************************************************************
;*************************************************************
;MAJOR EQUATES USED IN PROGRAM
;-----------------------------
;
```

```
;VALID DATA WINDOW-- INPUT ROUTINE. UTILIZED TO RECOGNIZE THAT
;INCOMING DATA IS VALID AND THAT THE NEXT TWO CYCLES SHOULD BE
;PROCESSED. TEST EQUATES PROVIDE A SECONDARY WINDOW FOR PROCESSING
;A TEST SIGNAL.
;
00B2        LSMIN   EQU     LOW  5298  ;WINDOW IS 80-110MS
0014        MSMIN   EQU     HIGH 5298;80/15.1US=5298
0075        LSMAX   EQU     LOW  7285  ;
001C        MSMAX   EQU     HIGH 7285;110MS/15.1MS=7285

;TEST WINDOW-- INPUT ROUTINE. VALID TEST FREQUENCY IS 1MHZ/2^14.
;=61.035HZ. TIME(PERIOD)=16.384MS AND PULSE DURATION IS HALF OR
;8.192MS PLUS OR MINUS .5%.
;
0018        TLMIN   EQU     LOW  536  ;WINDOW IS 8.147-8.238MS
0002        TMMIN   EQU     HIGH 536;
001E        TLMAX   EQU     LOW  542  ;(COUNT=T/15.2US)
0002        TMMAX   EQU     HIGH 542;

;VALID QUADRATURE WINDOWS-- USED IN THE SORT SUBROUTINE
;TO VERIFY THAT THE INPUT QUADRATURE PHASES ARE WITHIN RECOGNIZED
;LIMITS AND SET ERROR FLAGS IF NOT.
;           THERMAL REFERENCE LIMITS 80-110MS COUNT=5298-7285
00B2        TRLLS   EQU     LOW  5298 ;
0014        TRLMS   EQU     HIGH 5298;
0075        TRHLS   EQU     LOW  7285 ;
001C        TRHMS   EQU     HIGH 7285;
;
;           THERMAL DATA LIMITS 40-160MS
002C        TDLLS   EQU     LOW  1324        ;20MS/15.1US=1324
0005        TDLMS   EQU     HIGH 1324        ;
0012        TDHLS   EQU     LOW  15890       ;240MS/15.1US=15890
003E        TDHMS   EQU     HIGH 15890       ;
;
;           HEARTRATE REFERENCE LIMITS 130MS-300MS
;           (WITH  LOW BAT=130MS-199MS)
00A1        RRLLS   EQU     LOW  8609        ;50MS=8609 COUNTS
0021        RRLMS   EQU     HIGH 8609        ;
009B        RRHLS   EQU     LOW  19867       ;300MS=19867 COUNTS
004D        RRHMS   EQU     HIGH 19867       ;
;
;
;           EXTERNAL LOW BAT RECOGNITION RANGE 50MS-199MS
00A1        LBLLS   EQU     LOW  8609        ;130MS
0021        LBLMS   EQU     HIGH 8609        ;
007A        LBHLS   EQU     LOW  13178       ;199MS
0033        LBHMS   EQU     HIGH 13178       ;
;
;
;
;           HEARTRATE DATA LIMITS 28.8MS-375MS REPRESENTS 20-260 BPM.
;                   SIGNAL IS SECONDS/BEAT / 8 = (TIME/(2^13-2^10))
;                                           COUNT=1910 TO 24834
0076        RDLLS   EQU     LOW  1910        ;28.246MS/15.1US=1910
0007        RDLMS   EQU     HIGH 1910        ;
0002        RDHLS   EQU     LOW  24834       ;375MS/15.1US=24834
0061        RDHMS   EQU     HIGH 24834       ;
;
;           MIDPOINTS FOR TEST SIGNAL INSERTION AFTER VERIFICATION
;                   THESE VALUES WILL GIVE A TEST TEMP OF 36.7 C
;                   AND 98.1 F (AXILLARY NORMS) AND 60 HEART
004F        TRTVALL EQU     LOW  6223        ;TEMP REFERENCE TEST VALUE
0018        TRTVALH EQU     HIGH 6223        ;HIGH BYTE
008E        TDTVALL EQU     LOW  6286        ;TEMP DATA TEST VALUE
0018        TDTVALH EQU     HIGH 6286        ;HIGH BYTE
00E9        RRMIDL  EQU     LOW  14569       ;220MS BATTERY REFERENCE
```

```
0038            RRNIDH   EQU     HIGH 14669      ; HI BYTE
005D            RDNIDL   EQU     LOW 8541        ;125MS HEARTRATE DATA NOM
0021            RDNIDH   EQU     HIGH 8541       ;
                ;
                ;        COMPENSATION VALUE FOR TEMP CALCULATION
                ;                 VALUE CMPVA IS SUBTRACTED FROM CR AND CT. ALLOWING TEMPERATURE
                ;                 TO BE CALCULATED FROM THE EQN: T=M*((CR-CT)/(CR+CT-2CMPV))+98.6
0054            CMPVAL   EQU     LOW 596         ;LS BYTE
0002            CMPVAH   EQU     HIGH 596        ;MS BYTE
                ;-----------------------------------------------------------------
                ; LIMIT CALCULATIONS USE DATA FROM FOLLOWING DATA LOCATIONS
0028            LIMMIN   EQU     28H      ;
002A            TSTVAL   EQU     2AH      ;
002C            LIMMAX   EQU     2CH      ;
                ;
                ; FLAG REGISTERS -- DATA LOCATIONS:
0060            CFGFLG   EQU     60H      ;CONFIGURATION: bus=FF=NORM, 7F=CONTINUOUS, 3F=?
0061            HRFLG    EQU     61H      ;DISPLAY TEMPERATURE OR HEARTRATE (00 OR FF)
0062            THMERF   EQU     62H      ;THERMAL ERROR IF <> 00H
0063            FCFLG    EQU     63H      ;CENTIGRADE MODE=00, FAHRENHEIT MODE=FF
0064            RRERF    EQU     64H      ;HEARTRATE ERROR IF <> 00H
0065            TSTFLG   EQU     65H      ;TSTFLG SET WHEN VALID TEST SIGNAL DETECTED
0066            EXTINT   EQU     66H      ;EXTERNAL INTERRUPT RESET DELAY COUNTER
0067            LBERF    EQU     67H      ;LOW BATTERY ERROR FLAG
0068            TFLG     EQU     68H      ;98.6 TEMP FLAG, ALTERED BY COMPEA, USED BY TCALC
                ;-----------------------------------------------------------------
                ;-----------------------------------------------------------------
0000            ;
0000                     ORG     0H       ;PROGRAM LOADS AT LOCATION 0
0000 0459       START:   JMP     PROG     ;HARD RESET ENTERS AT LOC ZERO
0002 00                  NOP              ;FILL
0003 0410       INT3:    JMP     HRTRT    ;TOGGLE HEART RATE FLAG (EXT INT LOC 3)
0005 00                  NOP              ;FILL
0006 00                  NOP              ;FILL
0007 0429       INT7:    JMP     DISPLY   ;TIMER INTERRUPT (LOC 7), PHASE DISPLAY
0009 00                  NOP              ;
0010                     ORG     10H      ;
0010                                      ;
0010            ;****************************************************
0010            ; EXTERNAL INTERRUPT VECTORS TO HERE. THIS IS
0010            ; INTERRUPT FROM LOC 3 AND IS USED TO TOGGLE THE
0010            ; HEARTRATE/TEMP FLAG.  DISPLAY BUFFER IS ALSO UPDATED
0010            ; TO PRESENT APPROPRIATE MODE DATA.
0010 15         HRTRT:   DIS     I        ;ALLOW TIMER TO REENABLE INTERRUPT LOGIC
0011 D5                  SEL     RB1      ;USE ALT REGESTER BANK
0012 AE                  MOV     R6,A     ;SAVE ACCUM.
0013 B861                MOV     R0,#HRFLG
0015 F0                  MOV     A,@R0    ;GET HEARTRATE/TEMP FLAG
0016 961B                JNZ     HRTRT1   ;IF ITS ON TURN IT OFF
0018 37                  CPL     A        ;ELSE COMPLEMENT IT
0019 041C                JMP     HRTRT2   ;
001B 27         HRTRT1:  CLR     A        ;
001C A0         HRTRT2:  MOV     @R0,A    ;SAVE HRFLG
001D B83A                MOV     R0,#3AH  ;
001F 27                  CLR     A        ;
0020 A0                  MOV     @R0,A    ;
0021 18                  INC     R0       ;
0022 A0                  MOV     @R0,A    ;CLEAR LOCS 3A-3B AND LOAD BUFFER WITH
0023 B83A                MOV     R0,#3AH  ;THAT DATA (ZEROS)
0025 9430                CALL    LDDBUF   ;NEED TO CHANGE DISPLAY APPROPRIATELY
0027                             ;NOTE: TIMER INTRPT SERVICE REENABLES REGULAR
0027                     ;              INTERRUPT AFTER ALLOWING TIME FOR
0027                     ;              THAT PIN TO SETTLE HIGH AGAIN.
0027                     ;
0027 FE                  MOV     A,R6     ;RESTORE ACCUM.
0028 93                  RETR             ;RETURNING FROM INTERRUPT ROUTINE
0029                                      ;
0029            ;****************************************************
0029                     ;
```

```
0029                            ;TIMER COUNTER INTERRUPT VECTORS HERE
0029                            ;DISPLAY PHASE IS REVERSED, INT STAT UPDATED,
0029                            ;F/C SWITCH IS ALSO TESTED HERE AND FLAG IS UPDATED
0029                            ;
0029            DISPLY:
0029 D5                 SEL     RB1     ; SEL ALT REG BANK
002A AE                 MOV     R6,A    ; SAVE ACCUM.
002B B5                 CPL     F1      ; F1 CONTROLS LCD PHASE REVERSING
002C B83D               MOV     R0,#3DH ; LOC 3D IS FIRST DISPLAY BUFFER LOC
002E F0                 MOV     A,@R0   ;
002F 7632               JF1     DOUT1   ;COMPLEMENT DATA IF F1=0
0031 37                 CPL     A       ;
0032 39         DOUT1:  OUTL    P1,A    ;
0033 18                 INC     R0      ;GET SECOND DISPLAY LOC DATA NEXT
0034 F0                 MOV     A,@R0   ;
0035 7638               JF1     DOUT2   ;AND COMPLEMENT IF NECESSARY
0037 37                 CPL     A       ;
0038 3A         DOUT2:  OUTL    P2,A    ;THEN OUT
0039 18                 INC     R0      ;THIRD DISPLAY LOC
003A F0                 MOV     A,@R0   ;
003B 763E               JF1     DOUT3   ;SAME WITH THIRD DIGIT
003D 37                 CPL     A       ;
003E 02         DOUT3:  OUTL    BUS,A   ;THIRD PORT IS THE BUS REGISTER
003F                                    ;
003F                                    ;
003F B860               MOV     R0,#CFGFLG ;NOW GET CONFIG., IF NORMAL
0041 F0                 MOV     A,@R0   ;   THEN EXIT INTERRUPT
0042                    ;       ALLOW TOGGLE IN ANY MODE JB7    DISDNE ;
0042                                    ;ELSE PERFORM CONTINUOUS MODE FN.
0042 8650               JNI     MODINT  ;IF INTERRUPT LOW THEN SET COUNTER
0044 B866               MOV     R0,#EXTINT
0046 F0                 MOV     A,@R0.  ;ELSE IF HIGH AND CTR = 0 THEN
0047 C64D               JZ      ENABLE  ;ENSURE INTERRUPT IS ENABLED.
0049 07         DECRIN: DEC     A       ;OTHERWISE DECREMENT COUNTER
004A A0                 MOV     @R0,A   ;ONCE EVERY INTERRUPT
004B 9654               JNZ     DISDNE  ;IF NOT 0 THEN EXIT
004D 05         ENABLE: EN      I       ;ELSE ENABLE INT AND EXIT
004E 0454               JMP     DISDNE  ;

0050 B866       MODINT: MOV     R0,#EXTINT ;SET DELAY AT 10 TMR INTERRUPTS
0052 B00A               MOV     @R0,#10 ; APPROX 150MS.
0054                                    ;
0054 2345       DISDNE: MOV     A,#69   ;(256-N)*80US=T ; T=14.96MS N=69
0056 62                 MOV     T,A     ;SET TIMER INTERRUPT RATE
0057 FE                 MOV     A,R6    ;RESTORE ACCUMULATOR
0058 93                 RETR            ;THEN WE RETURN FROM INTERRUPT ROUTINE
           ;************************************************************
           ;============================================================
           ;                   MAIN PROGRAM ENTRY
           ;                   ------------------
0059                                    ;

0059 E5         PROG:   SEL     MB0     ;SELECT PROGRAM MEMORY PAGE 0
005A C5                 SEL     RB0     ;SELECT REGISTER BANK 0
005B 15                 DIS     I       ;
005C 35                 DIS     TCNTI   ;
005D 27         CLMEM:  CLR     A       ;
005E B87E               MOV     R0,#7EH ;CLEAR ALL OF MEMORY
0060 18         CLMEM1: INC     R0      ;MUST AVOID CLEARING R0 THOUGH
0061 A0                 MOV     @R0,A   ;MEM CLEARED 1-7FH
0062 C8                 DEC     R0      ;
0063 E860               DJNZ    R0,CLMEM1;
0065 35         TCHOIC: DIS     TCNTI   ;
0066 B863               MOV     R0,#FCFLG; FAHRENHEIT/CENTIGRADE TEST HERE
0068 27                 CLR     A       ;IF BU0=0 AND P10=1 THEN IF T0=0
0069 02                 OUTL    BUS,A   ; THEN ITS FAHRENHEIT, ELSE CENTIGRADE
006A 37                 CPL     A       ;
006B 39                 OUTL    P1,A    ;
006C 27                 CLR     A       ;
006D 3670               JT0     UPDATE  ;TO SET HIGH IS CENT.
006F 37                 CPL     A       ;ELSE MARK FOR FAHR=0FFH
```

```
0070 A0      UPDATE: MOV     @R0,A       ;CENTIGRADE MARKS FCFLG AT 00H
0071                                     ;NOW CHECK CONFIGURATION SWITCHES
0071 237F    CFGCK:  MOV     A,#07FH     ;RETRD FF=NORM, 7F=CONT MODE, 3F=?
0073 80              MOVX    A,@R0       ;READ THE BUS
0074 B860            MOV     R0,#CFGFLG  ;GET STORED CONFIGURATION LOC
0076 A0              MOV     @R0,A       ;AND SAVE CONFIG.
0077                                     ;NOW ENABLE TIMER AND HR INTERRUPTS
0077 05              EN      I           ;
0078 27              CLR     A           ;
0079 17              INC     A           ;
007A 62              MOV     T,A         ;LOAD TIMER WITH 01H FOR QUICK SVCE.
007B 25              EN      TCNTI       ;
007C 55              STRT    T           ;
007D                                     ;
007D 14C5            CALL    SELECT      ;DISPLAY BUFFER UPDATE
007F                                     ;
007F 27      CFG1:   CLR     A           ;LOOP ENTRY LOC FOR CONTINUOUS MODE.
0080 97              CLR     C           ;
0081 B820            MOV     R0,#20H     ;CONTINUOUS MODE CLEAR WORKSPACE
0083 BA1D            MOV     R2,#1DH     ;BUT LEAVE LOCS 3D-3F
0085 A0      CFG1A:  MOV     @R0,A       ;
0086 18              INC     R0          ;
0087 EA85            DJNZ    R2,CFG1A    ;
0089 B840            MOV     R0,#40H     ;AND CLEAR 40-5F (FLAGS AT 60+)
008B BA20            MOV     R2,#20H     ;
008D A0      CFG1B:  MOV     @R0,A       ;
008E 18              INC     R0          ;
008F EA8D            DJNZ    R2,CFG1B    ;
0091                                     ;
0091 341C            CALL    INPUT       ;NOW DO INPUT ROUTINE
0093                                     ;
0093 C697            JZ      CFGCK1      ;IF NO ERROR THEN CONTINUE
0095 C441            JMP     ERRR        ;ELSE ERROR TRAP
0097 B860    CFGCK1: MOV     R0,#CFGFLG  ;CK PORT CONFIG. AND BEEP IF NORM CFG
0099 F0              MOV     A,@R0       ;
009A F2A2            JB7     NORM11      ;
009C D2A4            JB6     CFG11       ;
009E 23F1            MOV     A,#0F1H     ;CFG 2 NOT ASSIGNED
00A0 C441            JMP     ERRR        ;
00A2 F435    NORM11: CALL    BEEP        ;BEEP REENABLES TCNTI WHEN DONE
00A4                                     ;
00A4 94AF    CFG11:  CALL    TST3        ;LOOK FOR VALID TEST SIGNAL
00A6                                     ;AND IF VALID AND OK THEN LOAD
00A6                                     ;98.6F/60BPM VALUES AND CONTINUE
00A6                                     ;ELSE CONTINUE WITHOUT LOADING
00A6                                     ;
00A6 34B8            CALL    SORT        ;SORT TEMP AND RR INTERVALS
00A8                                     ;
00A8 5400            CALL    COMPEN      ;COMPENSATION ROUTINES (ADJUSTS VALUES)
00AA                                     ;
00AA 5440            CALL    TRTST       ;TEST PULSEWIDTHS AND SET ERROR FLAGS
00AC B862            MOV     R0,#THMERF  ;CHECK THM ERROR BEFORE CALC
00AE F0              MOV     A,@R0       ;
00AF 96B5            JNZ     SKPTMP      ;
00B1                                     ;
00B1 54D0            CALL    TCALC       ;CALCULATE TEMPERATURE F & C.
00B3                                     ;
00B3 74B8            CALL    CCALC       ;
00B5                                     ;
00B5 B864    SKPTMP: MOV     R0,#RRERF   ;CHECK HEARTRATE ERROR BEFOR CALC
00B7 F0              MOV     A,@R0       ;
00B8 96BC            JNZ     SELTCH      ;
00BA                                     ;
00BA 74FD            CALL    HCALC       ;CALCULATE HEARTRATE IN BPM
00BC                                     ;FALL THROUGH TO SELTCH
00BC                                     ;IF HCALC ERROR THEN SELTCH WILL HANDLE
00BC                                     ;
00BC 14C5    SELTCH: CALL    SELECT      ;NOW SELECT RR,CTEMP OR FTEMP
00BE                                     ;
00BE B860            MOV     R0,#CFGFLG  ;
00C0 F0              MOV     A,@R0       ;
```

```
00C1 F2BC           JB7     SELTCH   ;IF NORMAL CONFIG THEN LOOP SELECT
00C3 047F           JMP     CFG1     ;ELSE LOOP TO INPUT ROUTINE

00C5                        ;END OF MAIN PROGRAM LINE
00C5                        ;********************************************
00C5                        ;SELECT SUBROUTINE
00C5                        ;SELECTS WHETHER TO UPDATE BUFFER WITH RR DATA
00C5                        ;OR TEMP (FAHR OR CENT) DATA, AND UPDATES BUFF
00C5                        ;INCLUDING THE LOADING OF ERROR DATA.
00C5                        ;
00C5 B867   SELECT:  MOV    R0,#LBERF    ;FIRST CHECK REMOTE BAT ERROR
00C7 F0              MOV    A,@R0    ;
00C8 C6CE            JZ     SELECT1  ;NO ERROR JUMP
00CA 9470            CALL   RBERLD   ;ELSE LOAD REMOTE BATTERY ERROR
00CC 241B            JMP    SELEND   ;AND END SELECT ROUTINE
00CE B861   SELECT1: MOV    R0,#HRFLG    ;NEXT CHECK HR OR TEMP FLAG
00D0 F0              MOV    A,@R0    ;
00D1 C6D5            JZ     TEMPSEL  ;SELECT TEMPERATURE
00D3 2402            JMP    HR1
00D5 B862   TEMPSEL: MOV    R0,#THMERF   ;NOW CHECK THERM ERROR FLAG
00D7 F0              MOV    A,@R0    ;
00D8 C6DE            JZ     TEMPS1   ;NO ERROR JUMP
00DA 9483            CALL   ERRLD    ;ELSE LOAD REGULAR ERROR
00DC 241B            JMP    SELEND   ;AND END SELECT SUBROUTINE
00DE B863   TEMPS1:  MOV    R0,#FCFLG    ;FINALLY IS IT FAHR OR CENT.
00E0 F0              MOV    A,@R0    ;
00E1 00              NOP
00E2 00              NOP
00E3 00              NOP
00E4 00              NOP
00E5 00              NOP
00E6 C6EA            JZ     TMP1     ;ZERO IS CENTIGRADE
00E8 04F6            JMP    TMP2     ;
00EA D44C   TMP1:    CALL   CLEAR    ;CENTIGRADE TEMPERATURE MODE
00EC B85A            MOV    R0,#5AH  ;AT MEM LOCATION 5AH, (LS BINARY)
00EE B920            MOV    R1,#20H  ;
00F0 D457            CALL   MOVE2    ;
00F2 D4DE            CALL   BINBCD   ;CVT TO BCD INTO LOC 22-24
00F4 2417            JMP    SELLD    ;AND LOAD BUFFER
00F6 D44C   TMP2:    CALL   CLEAR    ;FAHRENHEIT TEMPERATURE MODE
00F8 B858            MOV    R0,#58H  ;AT LOC 58H (LS BINARY)
00FA B920            MOV    R1,#20H  ;
00FC D457            CALL   MOVE2    ;
00FE D4DE            CALL   BINBCD   ;
0100 2417            JMP    SELLD    ;CVT AND LOAD
0102 B864   HR1:     MOV    R0,#RRERF    ;CHECK FOR HEARTRATE ERROR 1ST
0104 F0              MOV    A,@R0    ;
0105 C60B            JZ     HR11     ;NO ERROR JMP
0107 9483            CALL   ERRLD    ;ELSE LOAD BUFFER WITH REGULAR ERROR
0109 241B            JMP    SELEND   ;AND END SELECT SUBROUTINE
010B D44C   HR11:    CALL   CLEAR    ;
010D B85C            MOV    R0,#5CH  ;HR BINARY IN LOC 05CH (LS BINARY)
010F B920            MOV    R1,#20H  ;
0111 D457            CALL   MOVE2    ;
0113 D4DE            CALL   BINBCD   ;
0115 2417            JMP    SELLD    ;CVT AND LOAD
0117 B822   SELLD:   MOV    R0,#22H  ;LOAD BUFFER FROM BCD DATA AT LOC 22H
0119 9430            CALL   LDDBUF   ;
011B 83     SELEND:  RET             ;END SELECT SUBROUTINE
011C                        ;
011C                        ;********************************************
011C                        ;
011C                        ;INPUT DATA ROUTINE
011C                        ;TIMER UTILIZED TAKES 15.1US PER COUNT
011C                        ;    T=N*15US + 20US + 25US + 25US*INT[(N-255)/256]
011C                        ;      = 15.1US AT 6.00 MHZ XTAL FREQUENCY
011C                        ;********************************************
011C 4620   INPUT:   JNT1   INPUT1   ;LOOP TILL NOBURST CONDITION
011E 241C            JMP    INPUT    ;
0120 5624   INPUT1:  JT1    INPUT2   ;LOOP TILL BURST BEGINS
0122 2420            JMP    INPUT1   ;
0124 B832   INPUT2:  MOV    R0,#32H  ;FIRST BURST STARTS HERE
```

```
0126 B933            MOV     R1,#33H   ;LOC 32-33 IS COUNTER LS-MS
0128 BA01            MOV     R2,#1H    ;R2 IS INC NUMBER
012A 27              CLR     A         ;
012B A0              MOV     @R0,A     ;
012C A1              MOV     @R1,A     ;
012D 17              INC     A         ;
012E 463D    IN2A:   JNT1    INPUT3    ;LOOPING AND TIMING
0130 6A              ADD     A,R2      ;FIRST BURST CONDITION
0131 00              NOP               ;PRESERVE LOOP TIMING
0132 E62E            JNC     IN2A      ;
0134 21              XCH     A,@R1     ;
0135 6A              ADD     A,R2      ;
0136 F63B            JC      INOVER    ;IF OVERFLOW THEN START OVER
0138 21              XCH     A,@R1     ;
0139 242E            JMP     IN2A      ;
013B 241C    INOVER: JMP     INPUT     ;LETS START OVER
013D 20      INPUT3: XCH     A,@R0     ;SAVE LS PART BACK, CLEAR MEMORY AND
013E D44C            CALL    CLEAR     ; TEST IF BURST WAS VALID.
0140 B832            MOV     R0,#32H   ;LS,MSMIN AND LS,MSMAX ARE LIMITS
0142 B92A            MOV     R1,#TSTVAL
0144 D457            CALL    MOVE2     ;
0146 B928            MOV     R1,#LIMMIN
0148 B1B2            MOV     @R1,#LSMIN
014A 19              INC     R1        ;
014B B114            MOV     @R1,#MSMIN
014D B92C            MOV     R1,#LIMMAX
014F B175            MOV     @R1,#LSMAX
0151 19              INC     R1        ;
0152 B1FC            MOV     @R1,#MSMAX
0154 F400            CALL    LIMIT     ;NOW CK LIMITS
0156 E65C            JNC     VALID:    ;
0158 9496            CALL    TST1:     ;NOT REGULAR INPUT SO IS IT A TEST?
015A F63B            JC      INOVER    ;BURST INVALID, SO START OVER
015C 27      VALID:  CLR     A         ;WE HAVE A VALID BURST, SO PREPARE FOR
015D 97              CLR     C         ;NEXT BURST PHASE. 4 PHASES MEASURED
015E B820            MOV     R0,#20H   ;
0160 BA1D            MOV     R2,#1DH   ;
0162 D451            CALL    CLLP:     ;CLEAR LOC 20-3C
0164 B833            MOV     R0,#33H   ;SET POINTERS, PREPARE FOR MEASUREMENT
0166 B928            MOV     R1,#28H   ;@R1 ENTIRE CYCLE COUNTER, @R0 CURRENT
0168 BA01            MOV     R2,#1H    ;COUNTER(MS BYTE), R2=INCREMENTER, R3
016A BB02            MOV     R3,#2H    ;IS THE FULL CYCLE COUNTER (2 CYCLES)
016C 27              CLR     A         ;
016D 563B            JT1     INOVER    ;PREVIOUS CODE NOT COMPLETED DURING OFF PER.
016F 5679    INPUT4: JT1     INPUT5    ;WAIT NOW FOR 1ST BURST SUBPHASE
0171 6A              ADD     A,R2      ;WHILE COUNTING FULL CYCLE COUNTER
0172 E66F            JNC     INPUT4    ;
0174 21              XCH     A,@R1     ;FULL CYCLE COUNTER IS AT LOCATION 28
0175 6A              ADD     A,R2      ;
0176 21              XCH     A,@R1     ;INCREMENT IT (ROUGH 15 MICRSECONDS)
0177 246F            JMP     INPUT4    ;AND WAIT FOR NEXT BURST.
0179                                   ;FULL CYCLE OVERFLOW IN 1 SECOND
0179 35      INPUT5: DIS     TCNTI     ;DISABLE TIMER INTERRUPTS TO ENHANCE
017A                                   ;TIMING ACCURACY.
017A 15              DIS     I         ;DISABLE INTERRUPT (HR/TEMP SWITCH)
017B 27              CLR     A         ;DROP LS FULLCYCLE COUNT
017C 17              INC     A         ;
017D 468D    IN5A:   JNT1    INPUT6    ;
017F 6A              ADD     A,R2      ;THIS IS BURST1(OR BURST2 IF R3=1)
0180 00              NOP               ;PRESERVE LOOP TIMING
0181 E67D            JNC     IN5A      ;
0183 20              XCH     A,@R0     ;CARRY SO INC MS LOC
0184 6A              ADD     A,R2      ;
0185 20              XCH     A,@R0     ;
0186 21              XCH     A,@R1     ;AND INC FULLCYCLE COUNT
0187 6A              ADD     A,R2      ;
0188 F6B0            JC      ERBRST    ;THIS IS A BURST ERROR
018A 21      IN5B:   XCH     A,@R1     ;
018B 247D            JMP     IN5A      ;NOW LOOP
018D C8      INPUT6: DEC     R0        ;MUST SAVE LS PART OF BURSTCOUNT
```

```
018E 20                    XCH     A,@R0     ;
018F 27                    CLR     A         ;
0190 18                    INC     R0        ;INC R0 THREE TIMES TO NEXT MS LOC
0191 18                    INC     R0        ;
0192 18                    INC     R0        ;
0193 17                    INC     A         ;AND INIT A AT 1
0194 56A4      IN6A:       JT1     INPUT7    ;
0196 6A                    ADD     A,R2      ;HERE WE GO WITH A NOBURST COUNT
0197 00                    NOP               ;PRESERVE LOOP TIMING
0198 E694                  JNC     IN6A      ;
019A 20                    XCH     A,@R0     ;CARRY SO INC MS LOCATION
019B 6A                    ADD     A,R2      ;
019C 20                    XCH     A,@R0     ;
019D 21                    XCH     A,@R1     ;AND INC CYCLECOUNTER
019E 6A                    ADD     A,R2      ;
019F F6B4                  JC      ERNBST    ;ERROR NOBURST
01A1 21                    XCH     A,@R1     ;
01A2 2494                  JMP     IN6A      ;LOOP NOBURST CONDITION
01A4 C8        INPUT7:     DEC     R0        ;
01A5 20                    XCH     A,@R0     ;SAVE LS PART OF NOBURST
01A6 27                    CLR     A         ;
01A7 18                    INC     R0        ;AND INC R0 THREE TIMES
01A8 18                    INC     R0        ;TO NEXT BURST LOCATION
01A9 18                    INC     R0        ;
01AA 17                    INC     A         ;INIT A AT 1
01AB EB7D                  DJNZ    R3,IN5A   ;IF WE ONLY COLLECTED 1 BURST-NOBURST
01AD                                         ;PAIR THEN LOOP ONE TIME
01AD 27                    CLR     A         ;
01AE 25                    EN      TCNTI     ;REGULAR INTERRUPT WILL BE ENABLED BY
01AF                                         ; THE TIMER INTERRUPT ROUTINE.
01AF 83                    RET               ;ELSE WE HAVE COLLECTED OUR BURST
01B0                                         ;NOBURST PAIRS AND SAVED THEM INTO
01B0                                         ;LOCS 32-33, 34-45, 36-37 AND 38-39.
01B0                                         ;
01B0 25        ERBRST:     EN      TCNTI     ;REENABLE DISPLAY INTERRUPTS
01B1 2301                  MOV     A,#1H     ;INSERT ERROR CODE 1 (BURST ERROR)
01B3 83                    RET               ;ERROR CODE IN ACC
01B4 25        ERNBST:     EN      TCNTI     ;SAME AS BURST ERROR EXCEPT CODE 2
01B5 2302                  MOV     A,#02     ;
01B7 83                    RET               ;ERROR CODE IN ACC
01B8                                         ;
01B8                       ;*********************************************
01B8                                         ;
01B8                                         ;SORT SUBROUTINE
01B8                                         ; SORTS THE BURST-NOBURST PAIRS BY CHECKING
01B8                                         ;FOR BURST PULSEWIDTH LESS THAN TR MAX AND
01B8                                         ;CALLING THAT THE TEMPERATURE INTERVAL,
01B8                                         ;ASSIGNING THE OTHER TO THE RR INTERVAL.
01B8                                         ;THE TWO PAIRS ARE THEN SAVED IN LOC 40-47
01B8                                         ;AS TREF(40-41),TDAT(42-43),RREF(44-45),
01B8                                         ;AND RRDAT(46-47).
01B8                                         ;LIMITS ARE CHECKED NEXT AND THE COUNT ERROR
01B8                                         ;FLAGS ARE UPDATED. (THMERF, RRERF)
01B8                                         ;
01B8 D44C      SORT:       CALL    CLEAR     ;
01BA B862                  MOV     R0,#THMERF
01BC B000                  MOV     @R0,#00H;CLEAR ERROR FLAGS
01BE B864                  MOV     R0,#RRERF
01C0 B000                  MOV     @R0,#00H;
01C2                                         ;
01C2                                         ;
01C2 B832                  MOV     R0,#32H   ;
01C4 B920                  MOV     R1,#20H   ;
01C6 BA02                  MOV     R2,#2     ;
01C8 D45D                  CALL    MOVE      ;MOV BURST TO MINUEND (20-24)
01CA B824                  MOV     R0,#24H   ;
01CC B075                  MOV     @R0,#TRHLS      ;LOW BYTE MAXREF TEMP
01CE 18                    INC     R0        ;
```

```
01CF B01C              MOV     @R0,#TRHMS      ;MS MAXREF TEMP
01D1 D400              CALL    SUBBIN          ;NOW SUBTRACT. IF CARRY THEN THIS BURST
01D3 F6D7              JC      SORTA           ;IS THE TEMP INTERVAL.
01D5 24E1              JMP     SORTB           ;
01D7 B832    SORTA:    MOV     R0,#32H         ;
01D9 B940              MOV     R1,#40H         ;SORTA MOVES DAT TO 40-47 IN ORDER
01DB BA08              MOV     R2,#8H          ;
01DD D45D              CALL    MOVE            ;
01DF 24F1              JMP     SORTRET         ;DONE A
01E1 B832    SORTB:    MOV     R0,#32H         ;
01E3 B944              MOV     R1,#44H         ;
01E5 BA04              MOV     R2,#4H          ;SORTB REVERSES THE MAJOR PHASES BEFORE
01E7 D45D              CALL    MOVE            ;SAVING THEM AS TREF,TDAT,RREF,RRDAT
01E9 B836              MOV     R0,#36H         ;IN LOCS 40-47
01EB B940              MOV     R1,#40H         ;
01ED BA04              MOV     R2,#4H          ;
01EF D45D              CALL    MOVE            ;
01F1 83      SORTRET:  RET                     ;SORT ROUTINE COMPLETE
01F2                   ;************************************************
0200                   ORG     200H            ;
0200                                           ;
0200                                           ;COMPENSATION ROUTINE FOR BURST ONE-SHOT
0200                                           ;
0200 97      COMPEN:   CLR     C               ;
0201 BA02              MOV     R2,#2H          ;THIS LOOP TWICE (BOTH BURSTS)
0203 B840              MOV     R0,#40H         ;GET FIRST BURST
0205 2302    COMPE1:   MOV     A,#02H          ;ADD 2
0207 60                ADD     A,@R0           ;
0208 A0                MOV     @R0,A           ;
0209 E60E              JNC     COMPE2          ;IF CARRY THEN INC MS BYTE
020B 18                INC     R0              ;
020C 10                INC     @R0             ;
020D 97                CLR     C               ;
020E B844    COMPE2:   MOV     R0,#44H         ;GET SECOND BURST AND LOOP IF NEC
0210 EA05              DJNZ    R2,COMPE1       ;
0212                                           ;NOW DO NOBURSTS
0212 BB02              MOV     R3,#2           ;THIS LOOP TWICE (BOTH NOBURSTS)
0214 B842              MOV     R0,#42H         ;MINUEND POINTER
0216 D44C    COMPE3:   CALL    CLEAR           ;CLEAR SCRATCHPAD
0218 B842              MOV     R0,#42H         ;NOBURST COMPENSATION NOW
021A B920              MOV     R1,#20H         ;
021C D457              CALL    MOVE2           ;
021E B924              MOV     R1,#24H         ;
0220 B102              MOV     @R1,#02H        ;WILL SUBTRACT 2 COUNTS FROM NOBST
0222 D400              CALL    SUBBIN          ;
0224 B820              MOV     R0,#20H         ;
0226 B942              MOV     R1,#42H         ;
0228 D457              CALL    MOVE2           ;
022A D44C    COMPE4:   CALL    CLEAR           ;
022C B846              MOV     R0,#46H         ;
022E B920              MOV     R1,#20H         ;
0230 D457              CALL    MOVE2           ;
0232 B924              MOV     R1,#24H         ;
0234 B102              MOV     @R1,#02H        ;SUBTRACT 2 FROM SECOND NOBURST
0236 D400              CALL    SUBBIN          ;
0238 B820              MOV     R0,#20H         ;
023A B946              MOV     R1,#46H         ;
023C D457              CALL    MOVE2           ;
023E 97                CLR     C               ;
023F 83                RET                     ;DONE WITH COMPENSATION
0240                                           ;
0240                   ;************************************
0240                   ;PULSE WIDTH TESTS FOR INPUT DATA
0240                   ; USES LIMIT SUBROUTINE TO CHECK FOR
0240                   ; VALID INPUT DATA, AND UPDATES ERROR
0240                   ; FLAGS THMERF, RRERF IF INAPPROPRIATE LIMITS
0240                   ;
0240 B840    TRTST:    MOV     R0,#40H         ;POINT TO THERMAL REFERENCE
0242 B92A              MOV     R1,#TSTVAL
```

```
0244 D457          CALL    MOVE2   ;
0246 B928          MOV     R1,#LIMMIN
0248 B1B2          MOV     @R1,#TRLLS
024A 19            INC     R1      ;
024B B114          MOV     @R1,#TRLMS
024D B92C          MOV     R1,#LIMMAX
024F B175          MOV     @R1,#TRHLS
0251 19            INC     R1      ;
0252 B11C          MOV     @R1,#TRHMS
0254 F400          CALL    LIMIT   ;CHECK UPPER & LOWER LIMIT ON THM REF.
0256 E65B          JNC     TDTST   ;JUMP IF OK
0258 B862          MOV     R0,#THMERF      ;ELSE UPDATE ERROR FLAG
025A A0            MOV     @R0,A           ;LS NIBBLE LS 2 BITS
025B B842  TDTST:  MOV     R0,#42H ;THIS TEST IS THERMAL DATA COUNT TEST
025D B92A          MOV     R1,#TSTVAL
025F D457          CALL    MOVE2   ;
0261 B928          MOV     R1,#LIMMIN
0263 B12C          MOV     @R1,#TDLLS
0265 19            INC     R1      ;
0266 B105          MOV     @R1,#TDLMS
0268 B92C          MOV     R1,#LIMMAX
026A B112          MOV     @R1,#TDHLS
026C 19            INC     R1
026D B13E          MOV     @R1,#TDHMS
026F F400          CALL    LIMIT   ;CHECK UPPER & LOWER LIM ON THERM DAT
0271 47            SWAP    A       ;NOW UPDATE ERROR FLAG MS NIBBLE
0272 B862          MOV     R0,#THMERF
0274 40            ORL     A,@R0   ;(00 OK, 01=<LIMMIN, 02=>LIMMAX)
0275 A0            MOV     @R0,A   ;
0276 B844  RRTST:  MOV     R0,#44H ;RR REFERENCE PULSE TEST
0278 B92A          MOV     R1,#TSTVAL
027A D457          CALL    MOVE2   ;
027C B928          MOV     R1,#LIMMIN
027E B1A1          MOV     @R1,#RRLLS
0280 19            INC     R1      ;
0281 B121          MOV     @R1,#RRLMS
0283 B92C          MOV     R1,#LIMMAX
0285 B19B          MOV     @R1,#RRHLS
0287 19            INC     R1
0288 B14D          MOV     @R1,#RRHMS
028A F400          CALL    LIMIT   ;RR REFERENCE PULSE LIMITS CHECKED
028C B864          MOV     R0,#RRERF       ;UPDATE ERROR FLAG
028E A0            MOV     @R0,A   ;
028F B846  RDTST:  MOV     R0,#46H ;LAST TEST IS RR DATA LIMIT TEST
0291 B92A          MOV     R1,#TSTVAL
0293 D457          CALL    MOVE2   ;
0295 B928          MOV     R1,#LIMMIN
0297 B176          MOV     @R1,#RDLLS
0299 19            INC     R1      ;
029A B107          MOV     @R1,#RDLMS
029C B92C          MOV     R1,#LIMMAX
029E B102          MOV     @R1,#RDHLS
02A0 19            INC     R1      ;
02A1 B161          MOV     @R1,#RDHMS
02A3 F400          CALL    LIMIT   ;ACC CONTAINS F0H,F1H,OR F2H ON RETURN
02A5 B864          MOV     R0,#RRERF
02A7 47            SWAP    A       ;
02A8 40            ORL     A,@R0   ;
02A9 A0            MOV     @R0,A   ;SAVE FLAG STAT
02AA                       ;
02AA B849  LBTST:  MOV     R0,#44H ;TEST RREF FOR LOW BAT NOW
02AC B92A          MOV     R1,#TSTVAL
02AE D457          CALL    MOVE2   ;
02B0 B928          MOV     R1,#LIMMIN
02B2 B1A1          MOV     @R1,#LBLLS
02B4 19            INC     R1
02B5 B121          MOV     @R1,#LBLMS
02B7 B92C          MOV     R1,#LIMMAX
02B9 B17A          MOV     @R1,#LBHLS
02BB 19            INC     R1      ;
02BC B133          MOV     @R1,#LBHMS
```

```
02BE F400              CALL     LIMIT    ;IF NO CARRY THEN SET LOW BAT ERROR FLAG
02C0 96C8              JNZ      NOTLB    ;
02C2 B867              MOV      R0,#LBERF
02C4 B0FF              MOV      @R0,#0FFH;
02C6 44CD              JMP      LBTEND   ;
02C8 B867     NOTLB:   MOV      R0,#LBERF;
02CA 2300              MOV      A,#00H   ;
02CC A0                MOV      @R0,A    ;
02CD 27       LBTEND:  CLR      A        ;
02CE 97                CLR      C        ;
02CF 83                RET               ;THEN RETURN
02D0                                     ;
              ;**************************************************************
02D0          ;CALCULATION ROUTINES FOR FAHRENHEIT AND CENTIGRADE
02D0          ;TEMPERATURE FROM COUNT VALUES.
02D0          ;
02D0          ;THE GENERALIZED EQUATION FOR FTEMP CALCULATION AFTER CR AND CT
02D0          ;HAVE BEEN ALTERED BY COMPEA IS:
02D0          ;FTEMP = 98.6 + ((CR-CT/(CR+CT))*90
02D0          ;        WHERE CR=REFERENCE COUNT
02D0          ;              CT=THERMISTER COUNT
02D0          ;SINCE INTEGER ARITHMETIC IS USED, THE EQUATION IS
02D0          ;TRANSFORMED TO:
02D0          ;  20*FTEMP = 1972 + 1800*CR/(CR+CT) -1800*CT/(CR+CT)
02D0          ;AFTER TEMP IS CALCULATED, TFLAG IS CHECKED, DETERMINING WHETHER
02D0          ;OR NOT THE VALUE NEEDS TO BE COMPENSATED. IF SO (T>98.6 F)
02D0          ;THEN THE COMPENSATED TEMP IS CALCULATED FROM THE UNCOMPENSATED
02D0          ;TEMP BY THE EXPERIMENTALLY DERIVED EQUATION...
02D0          ;     T(new)=1.0645*[T(old)]-6.3607 (decimal)
02D0          ;HOWEVER, THE ACTUAL EQUATION USED BY THE PROGRAM IS...
02D0          ;     20*T(new)=1.0645*[20*T(old)]-127.214 (decimal)
02D0          ;THE ACCURACY IS PRESERVED BY USING A 4 DECIMAL PLACE FIXED POINT
02D0          ;FORMAT AND DIVIDING BY 10,000 (decimal) AT THE END OF CALCULATION
02D0          ;ALL COMPUTATION IS DONE IN BINARY AND CONVERTED TO
02D0          ;BCD AFTER COMPUTATION AND DIVISION OF RESULT BY 2
02D0          ;TO GIVE FTEMP IN TENTHS OF A DEGREE FAHRENHEIT.
02D0          ;
02D0          ;CALCULATION IS BROKEN INTO THE FOLLOWING SEGMENTS
02D0          ;WITH STORAGE IN THE INDICATED MEMORY LOCATIONS
02D0          ; CR            ;STORED IN LOC 40-41
02D0          ; CT            ;STORED IN LOC 42-43
02D0          ; RRREF         ;STORED IN LOC 44-45
02D0          ; RR            ;STORED IN LOC 46-47
02D0          ; A=CR*1800     ;STORED IN LOC (48-4B)
02D0          ; B=CT*1800     ;STORED IN LOC (4C-4F)
02D0          ; C=CR+CT       ;        "      50-51
02D0          ; D=A/C         ;        "      52-53
02D0          ; E=B/C         ;        "      54-55
02D0          ; F=1972+D      ;        "      56-57
02D0          ; G=F-E, H=G/2  ;        "      58-59
02D0          ;THIS IS DEG F IN TENTHS (BINARY)
02D0          ; CA=(5/9)*(F-32)        ;      5A-5B
02D0          ;CENTIGRADE TEMPERATURE HERE
02D0          ;HEARTRATE IN BPM BINARY        5C-5D
02D0                                     ;
02D0                                     ;
02D0 94EA     TCALC:   CALL     COMPEA   ;COMPENSATION CURVE FLATTENER
02D2 D44C              CALL     CLEAR    ;CLEAR SCRATCHPAD
02D4 B840     TCALCA:  MOV      R0,#40H  ;A=CR*1800
02D6 B920              MOV      R1,#20H  ;CR-->20-23    1800D -->26-27
02D8 D457              CALL     MOVE2    ;RESULT A-->20-24--->48-4B
02DA B926              MOV      R1,#26H  ;1800D=0708H
02DC B108              MOV      @R1,#08H;
02DE 19                INC      R1       ;
02DF B107              MOV      @R1,#07H;
02E1 D464              CALL     MLTBIN   ;
02E3 B820              MOV      R0,#20H
02E5 B948              MOV      R1,#48H  ;
02E7 D45B              CALL     MOVE4    ;NOW SAVE COMPUTATION A
02E9 D44C     TCALCB:  CALL     CLEAR    ;
```

```
02EB B842              MOV    R0,#42H  ; B=CT*1800
02ED B920              MOV    R1,#20H  ;
02EF D457              CALL   MOVE2    ;
02F1 B926              MOV    R1,#26H  ;
02F3 B108              MOV    @R1,#08H ;
02F5 19                INC    R1       ;
02F6 B107              MOV    @R1,#07H ;
02F8 D464              CALL   MLTBIN   ;
02FA B820              MOV    R0,#20H  ;
02FC B94C              MOV    R1,#4CH  ;
02FE D45B              CALL   MOVE4    ;RESULT B-->LOC(4C-4F)
0300 D44C      TCALCC: CALL   CLEAR    ;
0302 B840              MOV    R0,#40H  ;C=(CR+CT)
0304 B920              MOV    R1,#20H  ;
0306 D45B              CALL   MOVE4    ;
0308 B820              MOV    R0,#20H  ;
030A B922              MOV    R1,#22H  ;
030C BA02              MOV    R2,#2    ;
030E 97                CLR    C        ;
030F D439              CALL   ABIN1    ;ADD (20-21)+(22-23)-->20-21
0311 B820              MOV    R0,#20H  ;
0313 B950              MOV    R1,#50H  ;
0315 D457              CALL   MOVE2    ;RESULT C--->LOC(50-51)
0317 D44C      TCALCD: CALL   CLEAR    ;
0319 B848              MOV    R0,#48H  ;D=(A/C)  = (CR*1800)/(CR+CT)
031B B920              MOV    R1,#20H  ;
031D D45B              CALL   MOVE4    ;
031F B850              MOV    R0,#50H  ;
0321 B926              MOV    R1,#26H  ;
0323 D457              CALL   MOVE2    ;
0325 D497              CALL   DIVBIN   ; A/C
0327 C62B              JZ     TCALCDD  ;IF NO DIVIDE ERROR THEN CONTINUE
0329 64B7              JMP    TRETN    ;ELSE RETURN WITH CODE IN ACC
032B B828      TCALCDD:MOV    R0,#28H  ;RESULT(28-2B)-->(52-53) LS 2 BYTES
032D B952              MOV    R1,#52H  ;
032F D457              CALL   MOVE2    ;SAVE D---->LOC(52-53)
0331 D44C      TCALCE: CALL   CLEAR    ;
0333 B84C              MOV    R0,#4CH  ; E=(B/C)  =(CT*1800)/(CR+CT)
0335 B920              MOV    R1,#20H  ;
0337 D45B              CALL   MOVE4    ;
0339 B850              MOV    R0,#50H  ;
033B B926              MOV    R1,#26H  ;
033D D457              CALL   MOVE2    ;
033F D497              CALL   DIVBIN   ;
0341 C645              JZ     TCALCEE  ;IF NO DIVIDE ERROR THEN CONT
0343 64B7              JMP    TRETN    ;ELSE RETN WITH ERROR CODE IN ACC
0345 B828      TCALCEE:MOV    R0,#28H  ;
0347 B954              MOV    R1,#54H  ;
0349 D457              CALL   MOVE2    ;SAVE E-->LOC(54-55)
034B D44C      TCALCF: CALL   CLEAR
034D B852              MOV    R0,#52H  ; F=(D+1972)
034F B920              MOV    R1,#20H  ;
0351 D457              CALL   MOVE2    ;
0353 B824              MOV    R0,#24H  ;
0355 B0B4              MOV    @R0,#0B4H         ;1972D=07A0H
0357 18                INC    R0       ;
0358 B007              MOV    @R0,#07H ;
035A D431              CALL   ADDBIN   ;2 BYTE ADD
035C B820              MOV    R0,#20H  ;
035E B956              MOV    R1,#56H  ;
0360 D457              CALL   MOVE2    ;SAVE F --->LOC(56-57)
0362 D44C      TCALCG: CALL   CLEAR    ;
0364 B856              MOV    R0,#56H  ; G=(F-E)
0366 B920              MOV    R1,#20H  ;
0368 D457              CALL   MOVE2    ;
036A B854              MOV    R0,#54H  ;
036C B924              MOV    R1,#24H  ;
036E D457              CALL   MOVE2    ;
0370 D400              CALL   SUBBIN   ;
0372 B820              MOV    R0,#20H  ;
0374 B958              MOV    R1,#58H  ;
```

```
0376 D457              CALL    MOVE2   ;SAVE G --->LOC(58-59)
0378 B868    TCALCH:   MOV     R0,#TFLG;TEST TFLG
037A F0                MOV     A,@R0   ;
037B C6AC              JZ      T1      ;IF TFLG CLEAR, GO TO T1
037D D44C              CALL    CLEAR   ;CLEAR SCRATCHPAD
037F B858              MOV     R0,#58H ;ELSE TFLG SET, SO COMPENSATE...20*T(new)=[2995h*(20*T
0381 B926              MOV     R1,#26H ;MOVE 20*F(old) TO SCRATCHPAD 26-27
0383 D457              CALL    MOVE2
0385 B820              MOV     R0,#20H ;MOVE 2995H TO SCRATCHPAD 20-21
0387 B095              MOV     @R0,#95H;LOW BYTE
0389 18                INC     R0
038A B029              MOV     @R0,#29H;HIGH BYTE
038C D464              CALL    MLTBIN  ;2995H*[20*T(old)] NOW IN SCRATCHPAD 20-23
038E B824              MOV     R0,#24H ;MOVE 13694CH TO SCRATCHPAD 24-27
0390 B04C              MOV     @R0,#4CH;LOW BYTE
0392 18                INC     R0
0393 B069              MOV     @R0,#69H
0395 18                INC     R0
0396 B013              MOV     @R0,#13H
0398 18                INC     R0
0399 B000              MOV     @R0,#0  ;ZERO FOR HIGH BYTE
039B D400              CALL    SUBBIN  ;NUMERATOR NOW IN SCRATCHPAD 20-23
039D B826              MOV     R0,#26H ;MOVE 2710H TO SCRATCHPAD 26-27
039F B010              MOV     @R0,#10H;LOW BYTE
03A1 18                INC     R0
03A2 B027              MOV     @R0,#27H;HIGH BYTE
03A4 D497              CALL    DIVBIN  ;RESULT IN SCRATCHPAD 28-29
03A6 B828              MOV     R0,#28H ;MOV 20*F(new) BACK TO LOCATION 58-59
03A8 B958              MOV     R1,#58H
03AA D457              CALL    MOVE2
03AC D44C    T1:       CALL    CLEAR
03AE B859              MOV     R0,#59H ;DIVIDE BY 2 USING RIGHT SHIFT
03B0 BB02              MOV     R3,#2
03B2 D489              CALL    SHIFTR  ;
03B4 97                CLR     C       ;MAY BE CARRY
03B5                                   ;DEG F LOC(58-59) BIN FORM IN TENTHS
03B5 2300              MOV     A,#00   ;CLR ACCUM NO ERROR
03B7 83     TRETN:     RET             ;RETURN FROM TCALC
03B8                             ;*********************************************
03B8                                   ;CENTIGRADE TEMPERATURE CALCULATION
03B8                                   ;
03B8 D44C   CCALC:     CALL    CLEAR   ;NOW CALCULATE CENTIGRADE TEMPERATURE
03BA                                   ;(BINARY CALCULATIONS) IN TENTHS DEG
03BA B858   CCALCA:    MOV     R0,#58H ;FROM THE EQUATION C=(5*(F-32))/9
03BC B920              MOV     R1,#20H ;FIRST F-320  (SINCE IN TENTHS )
03BE D457              CALL    MOVE2   ;
03C0 B822              MOV     R0,#22H ; 320D=140H
03C2 B040              MOV     @R0,#40H;
03C4 18                INC     R0      ;
03C5 B001              MOV     @R0,#01H;
03C7 B820              MOV     R0,#20H ;
03C9 B922              MOV     R1,#22H ;
03CB BA02              MOV     R2,#2H  ;
03CD 97                CLR     C       ;PREPARE FOR CALLING SUBTRACT LOOP
03CE D415              CALL    SBIN1   ;
03D0 27     CCALCB:    CLR     A       ;
03D1 B822              MOV     R0,#22H ;MULT LOC(20-21) BY 5
03D3 A0                MOV     @R0,A   ;
03D4 18                INC     R0      ;
03D5 A0                MOV     @R0,A   ;
03D6 B826              MOV     R0,#26H ;
03D8 B005              MOV     @R0,#5H ;
03DA 18                INC     R0      ;
03DB A0                MOV     @R0,A   ; MULT 20-23 * LOC(26-27)-->20-23
03DC D464              CALL    MLTBIN  ;
03DE B820              MOV     R0,#20H ;
03E0 B93A              MOV     R1,#3AH ;
03E2 D45B              CALL    MOVE4   ;SAVE 5*(F-32)
03E4 D44C              CALL    CLEAR   ;
```

```
03E6 B83A           MOV     R0,#3AH ;
03E8 B920           MOV     R1,#20H ;
03EA D45B           CALL    MOVE4   ;
03EC B826           MOV     R0,#26H ;
03EE B009           MOV     @R0,#9H ;
03F0 18             INC     R0      ;
03F1 27             CLR     A       ;
03F2 A0             MOV     @R0,A   ;
03F3 D497           CALL    DIVBIN  ;DIVIDE BY 9 LAST
                                    ...
03F5 97             CLR     C       ;
03F6 B828           MOV     R0,#28H ;
03F8 B95A           MOV     R1,#05AH;
03FA D457           CALL    MOVE2   ;SAVE TENTHS OF DEGREES C IN LOC(5A-5B)
03FC 83             RET             ;CCALC COMPLETE
03FD                                ;
03FD                ;***************************************************
03FD                                ;
03FD                                ;CALCULATION ROUTINES FOR HEARTRATE
03FD                                ;HR(BPM)=(60SEC/MIN)*(1.031746032) / (COUNT*15.1uS*4*2)
03FD                                ;     =512,457D/COUNT=07D1C9H/COUNT
03FD                                ;SINCE THE HEART FREQUENCY IS MULTIPLIED BY 4 IN
                                      THE TRANSMITTER
03FD                                ;THE TIME INTERVAL CORRESPONDING TO THE HALF CYCLE WHICH
                                      IS ACTUAL!
03FD                                ;TRANSMITTED AND COUNTED IS DECREASED BY A FACTOR OF 4*2=8.
03FD                                ;1.031746032 IS AN EXPERIMENTALLY DERIVED COMPENSATION
                                      CONSTANT
03FD                                ;
03FD 27    HCALC:   CLR     A       ;
03FE 97             CLR     C       ;
03FF B820           MOV     R0,#20H ;512,457d = 7D1C9h
0401 B0C9           MOV     @R0,#0C9H;LS BYTE
0403 18             INC     R0      ;
0404 B0D1           MOV     @R0,#0D1H;NLS BYTE
0406 18             INC     R0      ;
0407 B007           MOV     @R0,#07H; BYTE 3
0409 18             INC     R0      ;
040A A0             MOV     @R0,A   ; MS BYTE IS ZERO
040B B926           MOV     R1,#26H ; DIVISOR WILL BE HR COUNT
040D B846           MOV     R0,#46H ; AT LOC 46
040F D457           CALL    MOVE2   ;
0411 D497           CALL    DIVBIN  ;DIVIDE 07D1C9H BY RRCNT=BPM BINARY
0413 C617           JZ      HCALCA  ;IF NO DIVIDE ERROR
0415 841F           JMP     HCRETN  ;ELSE RETURN WITH ERROR IN ACC
0417 B828  HCALCA:  MOV     R0,#28H ;NOW MOVE ANSWER FROM 28-29 TO 5C-5D
0419 B95C           MOV     R1,#5CH ;
041B D457           CALL    MOVE2   ;MOVING LS 2BYTES (MS 2 CHECK LATER)
041D 2300           MOV     A,#00   ;NO ERROR RETURN A CLEAR
041F 83    HCRETN:  RET             ; DONE WITH HR CALC
0420                                ;
0420                                ;
0420                ;***************************************************
0420                                ;
0420                ORG     420H    ;
0420                                ;BCD TO SEVEN SEG. LOOKUP TABLE
0420                                ;(also does binary to 7 seg)
0420 7E             DB      7EH     ;0
0421 0C             DB      0CH     ;1
0422 B6             DB      0B6H    ;2
0423 9E             DB      9EH     ;3
0424 CC             DB      0CCH    ;4
0425 DA             DB      0DAH    ;5
0426 FA             DB      0FAH    ;6
0427 0E             DB      0EH     ;7
0428 FE             DB      0FEH    ;8
0429 DE             DB      0DEH    ;9
042A EE             DB      0EEH    ;A
```

```
042B F8                   DB      0F8H    ;b
042C 72                   DB      072H    ;C
042D BC                   DB      0BCH    ;d
042E F2                   DB      0F2H    ;E
042F E2                   DB      0E2H    ;F

0430                              ;R IS 0A0H (SMALL R)
0430                              ;*********************************************
0430                              ;LOAD BUFFER SUBROUTINE
0430                              ;USED BY SELECT TO UPDATE DISPLAY BUFFER WITH
0430                              ;APPROPRIATE DATA. LOADS DATA FROM RO POINTER.
0430                              ;
0430 B961     LDDBUF: MOV    R1,#HRFLG;FIRST DETERMINE WHETHER TO DISPLAY
0432 F1               MOV    A,@R1    ;H(DP NOT SET) OR TEMP(DP SET)
0433 9637             JNZ    LDDBA    ;
0435 8443             JMP    LDBUF1   ;
0437 B93D     LDDBA:  MOV    R1,#3DH  ;H MODE - DON'T SET DP
0439 F0               MOV    A,@R0    ;
043A AA               MOV    R2,A
043B 530F             ANL    A,#0FH   ;
043D 0320             ADD    A,#20H   ;
043F A3               MOVP   A,@A     ;
0440 A1               MOV    @R1,A    ;
0441 844F             JMP    LDBUF2   ;
0443 B93D     LDBUF1: MOV    R1,#3DH  ;TEMP MODE - SET DP ON LS DIGIT
0445 F0               MOV    A,@R0    ;GET LS DIGIT
0446 AA               MOV    R2,A     ;SAVE IT TEMPORARILY
0447 530F             ANL    A,#0FH   ;AND MASK OFF UPPER NIBBLE
0449 0320             ADD    A,#20H   ;NOW CONVERT TO SEVEN SEGMENT DATA THROUGH
044B A3               MOVP   A,@A     ;LOOKUP TABLE
044C 4301             ORL    A,#01H   ;OUT TO DISPLAY WITH DP SET
044E A1               MOV    @R1,A    ;
044F                                  ;
044F 19       LDBUF2: INC    R1       ;
0450 FA               MOV    A,R2     ;NOW DO UPPER NIBBLE
0451 47               SWAP   A        ;
0452 530F             ANL    A,#0FH   ;
0454 0320             ADD    A,#20H   ;
0456 A3               MOVP   A,@A     ;
0457 A1               MOV    @R1,A    ;
0458                                  ;
0458 18               INC    R0       ;
0459 19               INC    R1       ;
045A F0               MOV    A,@R0    ;THIRD DIGIT IS NEXT
045B AA               MOV    R2,A     ;SAVE UPPER NIB
045C 530F             ANL    A,#0FH   ;
045E 0320             ADD    A,#20H   ;
0460 A3               MOVP   A,@A     ;
0461 A1               MOV    @R1,A    ;
0462                                  ;
0462 FA               MOV    A,R2     ;NOW CHECK IF HUNDREDS OR NOT
0463 47               SWAP   A        ;THIS SHOULD BE ZERO IN CENTIGRADE
0464 530F             ANL    A,#0FH   ;
0466 9669             JNZ    HDRDS    ;
0468 83               RET             ;
0469 B93E     HDRDS:  MOV    R1,#3EH  ;GET HDRDS DIG.
046B F1               MOV    A,@R1    ;
046C 4301             ORL    A,#01H   ;SET LS BIT
046E A1               MOV    @R1,A    ;THEN PUT IT BACK IN THE BUFFER
046F 83               RET             ;ALL DONE
0470                                  ;
0470 B93F     RBERLD: MOV    R1,#3FH  ;REMOTE BATTERY ERROR LOAD BUFFER
0472 B1A0             MOV    @R1,#0A0H        ;"r"
0474 C9               DEC    R1       ;3F IS MS DIG, 3D IS LS
0475 B1F8             MOV    @R1,#0F8H        ;"b"
0477 C9               DEC    R1       ;
```

```
0478 B861              MOV    R0,#HRFLG ;NOW CHECK AND SET OR NOT DP
047A F0                MOV    A,@R0    ;
047B 9680              JNZ    HRERB    ;
047D B181              MOV    @R1,#81H ;DP SET ;".-F"
047F 83                RET             ;
0480 B180      HRERB:  MOV    @R1,#080H         ;" -H"
0482 83                RET             ;RETURN FROM LOADING BUFFER
0483 B93F      ERRLD:  MOV    R1,#3FH ;REGULAR ERROR BUFFER LOADER (ERR)
0485 B1F2              MOV    @R1,#0F2H         ;"E"
0487 C9                DEC    R1       ;
0488 B1A0              MOV    @R1,#0A0H         ;"r"
048A C9                DEC    R1       ;
048B B861              MOV    R0,#HRFLG ;NOW CHECK DP OR NOT
048D F0                MOV    A,@R0    ;
048E 9693              JNZ    HRERC    ;
0490 B1A1              MOV    @R1,#0A1H         ;".r"
0492 83                RET
0493 B1A0      HRERC:  MOV    @R1,#0A0H         ;"r"
0495 83                RET             ;RETURN FROM ERROR LOAD
0496                   ;
0496                   ;**************************************************************
0496                   ;
0496                   ; TEST SIGNAL PROCESSING ROUTINES
0496                   ;   DETERMINES THE VALIDITY OF TEST SIGNAL
0496                   ;
0496 D44C      TST1:   CALL   CLEAR    ;TEST IF A TEST INPUT SIGNAL(FROM INPUT ROUTINE)
0498 B832              MOV    R0,#32H  ;
049A B92A      TST2:   MOV    R1,#TSTVAL
049C D457              CALL   MOVE2    ;
049E B928              MOV    R1,#LIMMIN
04A0 B118              MOV    @R1,#TLMIN
04A2 19                INC    R1       ;
04A3 B102              MOV    @R1,#TMMIN        ;
04A5 B92C              MOV    R1,#LIMMAX        ;
04A7 B11E              MOV    @R1,#TLMAX        ;
04A9 19                INC    R1       ;
04AA B102              MOV    @R1,#TMMAX        ;
04AC F400              CALL   LIMIT    ;
04AE 83                RET             ;RETURN WITH CARRY IF OUT OF LIMITS
04AF                   ;
04AF D44C      TST3:   CALL   CLEAR    ;TEST IF 4 INPUT PHASES ARE WITHIN LIMITS
04B1                            .      ;ESTABLISHED WITH EQUATES USED IN TST2
04B1 B832              MOV    R0,#32H  ;
04B3 949A              CALL   TST2     ;
04B5 F6E8              JC     NOTST    ;
04B7 D44C              CALL   CLEAR    ;
04B9 B834              MOV    R0,#34H  ;
04BB 949A              CALL   TST2     ;
04BD F6E8              JC     NOTST    ;
04BF D44C              CALL   CLEAR    ;
04C1 B836              MOV    R0,#36H  ;
04C3 949A              CALL   TST2     ;
04C5 F6E8              JC     NOTST    ;
04C7 D44C              CALL   CLEAR    ;
04C9 B838              MOV    R0,#38H  ;
04CB 949A              CALL   TST2     ;
04CD F6E8              JC     NOTST    ;
04CF
04CF B932              MOV    R1,#32H ;TEST PULSE SEQ IS OK--- NOW FILL TESTVALS
04D1 B14F              MOV    @R1,#TRTVALL      ;THERMAL REFERENCE
04D3 19                INC    R1       ;
04D4 B118              MOV    @R1,#TRTVALH
04D6 19                INC    R1       ;
04D7 B18E              MOV    @R1,#TDTVALL      ;THERMAL DATA
04D9 19                INC    R1       ;
04DA B118              MOV    @R1,#TDTVALH
04DC 19                INC    R1       ;
04DD B1E9              MOV    @R1,#RRMIDL       ;HEARTRATE REF PULSE
04DF 19                INC    R1       ;
04E0 B138              MOV    @R1,#RRMIDH       ;
```

```
04E2 19              INC     R1      ;
04E3 B15D            MOV     @R1,#RDMIDL    ;HEARTRATE DATA
04E5 19              INC     R1      ;
04E6 B121            MOV     @R1,#RDMIDH    ;
04E8 97      NOTST:  CLR     C       ;
04E9 83              RET             ;RETURN FROM STUFFING TEST DATA
04EA
04EA         ;-------------------------------------------------------
04EA         ;COMPEA SUBTRACTS CMPVA FROM CR AND CT BEFORE TEMP
04EA         ; CALCULATION.
04EA D44C    COMPEA: CALL    CLEAR   ;FIRST TEST CR>CT
04EC B840            MOV     R0,#40H ;CR
04EE B920            MOV     R1,#20H ;
04F0 D457            CALL    MOVE2   ;
04F2 B842            MOV     R0,#42H ;CT
04F4 B924            MOV     R1,#24H ;
04F6 D457            CALL    MOVE2   ;
04F8 B824            MOV     R0,#24H ;INCREMENT CT SO THAT CARRY IS GENERATED IF CR=CT
04FA 10              INC     @R0
04FB D400            CALL    SUBBIN  ;IF CR<=CT THEN CARRY IS GENERATED, I.E. T<=98.6
04FD 00              NOP             ;THESE ARE FILLS WHICH MUST BE PRESENT IN ORDER
04FE 00              NOP             ;FOR THE JC COMMAND DIRECTLY BELOW TO HAVE ITS
04FF 00              NOP             ;DESTINATION (CLRTFLG) ON SAME PAGE. [WEAK LANGUAGE]
0500 F608            JC      CLRTFLG ;IF CARRY GO TO CLRTFLG
0502 B868            MOV     R0,#TFLG;ELSE SET IT
0504 B0FF            MOV     @R0,#0FFH
0506 A40C            JMP     C1      ;AND GO TO C1
0508 B868    CLRTFLG:MOV     R0,#TFLG;CLEAR TFLG
050A B000            MOV     @R0,#0
050C
050C D44C    C1:     CALL    CLEAR   ;
050E B840            MOV     R0,#40H ;WILL SUB CMPVA FROM CR AND CT
0510 B920            MOV     R1,#20H ;
0512 D457            CALL    MOVE2   ;
0514 B924            MOV     R1,#24H ;
0516 B154            MOV     @R1,#CMPVAL
0518 19              INC     R1      ;
0519 B102            MOV     @R1,#CMPVAH; HIGH AND LOW BYTES
051B D400            CALL    SUBBIN  ;CMPVA IS HIGH BYTE SUBTRACT
051D B820            MOV     R0,#20H ;
051F B940            MOV     R1,#40H ;
0521 D457            CALL    MOVE2   ;MOVE IT BACK
0523                         ;
0523 D44C            CALL    CLEAR   ;NOW DO CT AT LOC 42H
0525 B842            MOV     R0,#42H ;
0527 B920            MOV     R1,#20H ;
0529 D457            CALL    MOVE2   ;
052B B924            MOV     R1,#24H ;
052D B154            MOV     @R1,#CMPVAL
052F 19              INC     R1      ;
0530 B102            MOV     @R1,#CMPVAH
0532 D400            CALL    SUBBIN  ;
0534 B820            MOV     R0,#20H ;
0536 B942            MOV     R1,#42H ;
0538 D457            CALL    MOVE2   ;MOVE CT BACK
053A 83              RET             ;DONE...
             ;-------------------------------------------------------

INCLUD ANDESUB.ASM
053B         SUBTTL * ANDESUB.ASM - ANDE4 SUBROUTINES *

;**************************************************************
053B         ;FILE ANDESUB.ASM -- SUBROUTINES FOR ANDE4.ASM PROG
053B                 ;
0600            ORG     0600H   ;
0600                    ;BEGINNING OF SECOND 1K (8049)
0600                    ;
             ;**************************************************************
0600            ;       *** SUBBIN SUBROUTINE ***
```

```
0600                            ;SUBROUTINE TO SUBTRACT THE FOUR BYTE BINARY
0600                            ;NUMBER IN LOCS 24-27 FROM THE BINARY NUMBER
0600                            ;IN 20-23.  RESULT IN 20-23.  RETURN CARRY BIT
0600                            ;IS SET IF VALUE IN 24-27 WAS LARGER.
0600                            ;PRESERVES REGISTERS 0,1, AND 2.
0600                            ;
0600 D408       SUBBIN: CALL    SAVREG  ;SAVE R0,R1,R2 IN R5,R6,R7
0602 97                 CLR     C       ;
0603 D415               CALL    SBIN1   ;
0605 D42A               CALL    GETREG  ;GET REG R0,R1,R2 FROM R5,R6,R7
0607 83                 RET             ;SUBTRACT ROUTINE DONE
0608                            ;
0608 F8         SAVREG: MOV     A,R0    ;SAVE R0,R1,R2 IN R5,R6,R7
0609 AD                 MOV     R5,A    ;AND SET UP POINTERS R0=20H,R1=24H,R2=4
060A F9                 MOV     A,R1    ;
060B AE                 MOV     R6,A    ;
060C FA                 MOV     A,R2    ;
060D AF                 MOV     R7,A    ;
060E B820               MOV     R0,#20H ;MINUEND POINTER R0
0610 B924               MOV     R1,#24H ;SUBTRAHEND PTR. R1
0612 BA04               MOV     R2,#4H  ;BYTE COUNTER    R2
0614 83                 RET             ;
0615                            ;

0615 F1         SBIN1:  MOV     A,@R1   ;ONES COMPLEMENT,INC LS BYTE AND ADD
0616 37                 CPL     A       ;
0617 17                 INC     A       ;
0618 60                 ADD     A,@R0   ;
0619 A0                 MOV     @R0,A   ;AND SAVE BYTE BACK
061A 19         SBIN2:  INC     R1      ;
061B 18                 INC     R0      ;
061C EA20               DJNZ    R2,SBIN3;IF ZERO THEN THIS WAS A ONE BYTE OPERATION
061E A7                 CPL     C       ;
061F 83                 RET             ;AND WE RETURN TO CALLING ROUTINE
0620 F1         SBIN3:  MOV     A,@R1   ;
0621 37                 CPL     A       ;ADD WITH CARRY
0622 70                 ADDC    A,@R0   ;
0623 A0                 MOV     @R0,A   ;
0624 18                 INC     R0      ;
0625 19                 INC     R1      ;
0626 EA20               DJNZ    R2,SBIN3;
0628 A7                 CPL     C       ;
0629 83                 RET             ;RETURN FROM SUB

062A                            ;
062A FD         GETREG: MOV     A,R5    ;
062B A8                 MOV     R0,A    ;
062C FE                 MOV     A,R6    ;
062D A9                 MOV     R1,A    ;
062E FF                 MOV     A,R7    ;
062F AA                 MOV     R2,A    ;
0630 83                 RET             ;AND RETURN
0631                            ;
0631                            ;*******************************************
0631                            ;
0631                            ;   **** ADDBIN SUBROUTINE ****
0631                            ;SUBROUTINE TO ADD THE FOUR BYTE BINARY NUMBER
0631                            ;IN LOC 24-27 TO THE BIN NUMBER IN 20-23.
0631                            ;RESULT IN 20-23. RETURN CARRY BIT SET IF
0631                            ;
0631 D408       ADDBIN: CALL    SAVREG  ;PRESERVE REGISTERS 0, 1, AND 2
0633 97                 CLR     C       ;NOW ADD THE NUMBERS TOGETHER BYTE BY BYTE
0634 D439               CALL    ABIN1   ;PERFORM ADDITION
0636 D42A               CALL    GETREG  ;RESTORE REG 0,1,2
0638 83                 RET             ;RETURN FROM ADD ROUTINE
0639                            ;
0639 F1         ABIN1:  MOV     A,@R1   ;TERM1 TO ACCUMULATOR
063A 70                 ADDC    A,@R0   ;PERFORM ADDITION INCLUDING CARRY IF ANY
063B A0                 MOV     @R0,A   ;AND MOVE THIS BYTE TO MEMORY
063C 18                 INC     R0      ;INCREMENT POINTERS
```

```
063D 19              INC     R1      ;
063E EA39            DJNZ    R2,ABIN1;AND TEST LOOP
0640 83              RET             ;RETURN FROM LOOP
0641                         ;
0641                         ;*******************************************
0641                         ; ERROR ROUTINE
0641                         ; VECTORS TO SELTCH AFTER UPDATING ERROR FLGS
0641                         ;
0641 B862    ERRR:   MOV     RO,#THMERF      ;SET ERROR FLAGS
0643 BOFF            MOV     @RO,#OFFH       ;WITH FFH
0645 B864            MOV     RO,#RRERF
0647 BOFF            MOV     @RO,#OFFH       ;
0649 25              EN      TCNTI   ;
064A 04BC            JMP     SELTCH  ;JUMP TO SELECTOR ROUTINE
064C                         ;*******************************************
064C                         ;       *** CLEAR ***
064C                         ;CLEARS MEMORY LOCATION 20-27 + CARRY
064C BA08    CLEAR:  MOV     R2,#08H ;
064E 27              CLR     A
064F B820            MOV     RO,#20H ;
0651 AO      CLLP:   MOV     @RO,A   ;
0652 18              INC     RO      ;
0653 EA51            DJNZ    R2,CLLP ;
0655 97              CLR     C       ;
0656 83              RET             ;RETURN FROM CLEAR SUBROUTINE
0657                         ;
0657                         ;*******************************************
0657                         ;MOVE DATA ROUTINES
0657                         ;
0657 BA02    MOVE2:  MOV     R2,#2H  ;
0659 C45D            JMP     MOVE    ;
065B BA04    MOVE4:  MOV     R2,#4H  ;
065D FO      MOVE:   MOV     A,@RO   ;MOVE DATA FROM RO PTR TO R1 POINTER
065E A1              MOV     @R1,A   ;
065F 18              INC     RO      ;
0660 19              INC     R1      ;
0661 EA5D            DJNZ    R2,MOVE ;
0663 83              RET             ;
0664                         ;
0664                         ;
0664                         ;*******************************************
0664                         ;BINARY MULTIPLICATION ROUTINE
0664                         ;
0664                         ; DBLMLT LOC 20-23 * LOC 26-27 --> LOC 20-25
0664                         ; USES RO-R4 AND ADLP FROM ADDITION ROUTINE
0664                         ; ------ ------  ------ ------ ------ ------
0664                         ;( 25  )( 24  )(  23  )( 22  )(  21 )(  20 )
0664                         ; ------ ------  ------ ------ ------ ------
0664                         ;  ^  ADD  ^   ----> MULTIPLIER
0664                         ; ------ ------
0664                         ;(  27 )(  26 )
0664                         ; ------ ------
0664                         ;   MULTIPLICAND
0664                         ;
0664 27      MLTBIN: CLR     A       ;
0665 97              CLR     C       ;
0666 B824            MOV     RO,#24H ;CLEAR 24-25
0668 AO              MOV     @RO,A   ;
0669 18              INC     RO      ;
066A AO              MOV     @RO,A   ;
066B BC20            MOV     R4,#32  ;WILL SHIFT 20-25 RIGHT 32 BITS
066D 97              CLR     C       ;
066E BB06    MBIN1:  MOV     R3,#6   ;SHIFT 6 BYTES AT 20 RIGHT ONE BIT
0670 B825            MOV     RO,#25H ;
0672 D489            CALL    SHIFTR  ;RO DECREMENTS ON RIGHT SHIFT
0674 E67F            JNC     MBIN3   ;NO CARRY, NO ADD
0676 97              CLR     C       ; ELSE ADD MULTIPLICAND(26-27) TO 24-25
0677 B824            MOV     RO,#24H ;
0679 B926            MOV     R1,#26H ;
067B BA02            MOV     R2,#2H  ;
```

```
067D D439            CALL    ABIN1   ;
067F EC6E   NBIN3:   DJNZ    R4,NBIN1;NOW LOOP TILL DONE
0681 B825            MOV     R0,#25H ; ONE FINAL SHIFT RIGHT
0683 BB06            MOV     R3,#6H  ;
0685 D489            CALL    SHIFTR  ;
0687 97              CLR     C       ;DON'T WANT CARRY ON RETURN
0688 83              RET             ;RESULT STORED IN 20-23
0689
0689                 ;*******************************************
0689                 ;SHIFT SUBROUTINES
0689                 ;SHIFTR: R0=MS BYTE, R3=LENGTH
0689                 ;
0689 F0     SHIFTR:  MOV     A,@R0   ;SHIFTS @R0 TO @R0-R3 TO RIGHT 1 BIT
068A 67              RRC     A       ; INCLUDES CARRY IN, CARRY OUT.
068B A0              MOV     @R0,A   ;
068C C8              DEC     R0      ;
068D EB89            DJNZ    R3,SHIFTR
068F 83              RET             ;
0690                 ;SHIFTL: R0=LS BYTE, R3=LENGTH
0690 F0     SHIFTL:  MOV     A,@R0   ;SHIFTS @R0 TO @R0+R3 TO LEFT 1 BIT
0691 F7              RLC     A       ;INCLUDES CARRY IN, CARRY OUT.
0692 A0              MOV     @R0,A   ;
0693 18              INC     R0      ;
0694 EB90            DJNZ    R3,SHIFTL
0696 83              RET             ;
0697
0697                 ;*******************************************
0697                 ;BINARY DIVIDE ROUTINE
0697                 ;
0697                 ;
0697                 ; DIVIDEND(20-23)/DIVISOR(24-25)--->
0697                 ; QUOTIENT(26-29)
0697                 ;
0697                 ; QUOTIENT  <SHFT<   :   <-- DIVIDEND--<SHFT<
0697                 ; 2B   2A   29   28  :  25  24  23  22  21  20
0697                 ;                    ^  :   ^   ^
0697                 ;                       INC:  SUBT.
0697                 ;                          : (26-27)
0697                 ;                             DIVISOR
0697                 ;
0697 27     DIVBIN:  CLR     A       ;
0698 97              CLR     C       ;
0699 BC20            MOV     R4,#32  ;32 SHIFTS LEFT ARE REQUIRED.
069B B824            MOV     R0,#24H ;CLEAR LOCS 24-25
069D A0              MOV     @R0,A   ;
069E 18              INC     R0      ;
069F A0              MOV     @R0,A   ;
06A0 B828            MOV     R0,#28H ;AND CLEAR 28-2B
06A2 BA04            MOV     R2,#4H  ;
06A4 A0     DCLR:    MOV     @R0,A   ;
06A5 18              INC     R0      ;
06A6 EAA4            DJNZ    R2,DCLR ;
06A8 B820   DVBIN1:  MOV     R0,#20H ;SHIFT DIVISOR LEFT 1 BIT
06AA BB06            MOV     R3,#6H  ;
06AC D490            CALL    SHIFTL  ;
06AE                 ; GENERATES ERROR ON LOW HR;;   JC      DVERR
06AE B828            MOV     R0,#28H ;SHIFT QUOTIENT LEFT 1 BIT
06B0 BB04            MOV     R3,#4H  ;
06B2 D490            CALL    SHIFTL  ;
06B4 F6D5            JC      DVERR   ;
06B6 B824            MOV     R0,#24H ;NOW WE SUBTRACT
06B8 B926            MOV     R1,#26H ;
06BA BA02            MOV     R2,#2   ;
06BC D415            CALL    SBIN1   ;
06BE E6CC            JNC     DVINC   ;IF NO CARRY THEN INC QUOTIENT
06C0 97              CLR     C       ;ELSE ADD BACK
06C1 B824            MOV     R0,#24H ;
06C3 B926            MOV     R1,#26H ;
```

```
06C5 BA02        MOV    R2,#2    ;
06C7 D439        CALL   ABIN1    ;
06C9 97          CLR    C        ;
06CA C4D0        JMP    DVLPCK   ;AND CHECK LOOP STATUS
06CC B928  DVINC: MOV   R1,#28H  ;
06CE 11          INC    @R1      ;SET LS QUOTIENT BIT
06CF 00          NOP             ;
06D0 ECA8  DVLPCK: DJNZ R4,DVBIN1 ;32 TIMES
06D2 2300        MOV    A,#00    ;CLEAR A -- EVERYTHING OK
06D4 83          RET             ;THEN ITS ALL DONE

06D5 2344  DVERR: MOV   A,#44H   ;44 IS DIVIDE ERROR CODE
06D7 B862        MOV    R0,#THMERF   ;UPDATE ERROR FLAGS
06D9 A0          MOV    @R0,A    ;
06DA B864        MOV    R0,#RRERF    ;(BOTH)
06DC A0          MOV    @R0,A    ;
06DD 83          RET             ;AND RETURN TO CALLING ROUTINE
06DE             ;       OLD ---> JMP    ERRR    ;
06DE             ;
06DE             ;
06DE             ;
06DE             ;*********************************************************
06DE             ;
06DE             ;   *** BINBCD SUBROUTINE ***
06DE             ;CONVERT THE UNSIGNED TWO BYTE BINARY VALUE
06DE             ;STORED IN 20-21 TO A PACKED BCD NUMBER IN
06DE             ;22-24. SINCE THE LARGEST POSSIBLE INPUT
06DE             ;VALUE IS 65000, AT MOST THREE OF THE FOUR
06DE             ;DESTINATION BYTES WILL BE UTILIZED.
06DE             ;       CARRY IS SET ON RETURN IF ERROR.
06DE             ;
06DE 27    BINBCD: CLR  A        ;
06DF B822        MOV    R0,#22H  ;
06E1 A0          MOV    @R0,A    ;
06E2 18          INC    R0       ;
06E3 A0          MOV    @R0,A    ;
06E4 18          INC    R0       ;
06E5 A0          MOV    @R0,A    ;CLEARED 23-25
06E6 BC10        MOV    R4,#16   ;LOOP COUNTER
06E8 97    BCD02: CLR   C        ;
06E9 B820        MOV    R0,#20H  ;
06EB BB02        MOV    R3,#2    ;
06ED D490        CALL   SHIFTL   ;SHIFT 20-21 LEFT 1 BIT
06EF B922        MOV    R1,#22H  ;POINT TO DEST
06F1 BD03        MOV    R5,#3    ;DOES 3 BYTES ON BCD #
06F3 F0    BCD03: MOV   A,@R0    ;
06F4 70          ADDC   A,@R0    ;
06F5 57          DA     A        ;
06F6 A0          MOV    @R0,A    ;
06F7 18          INC    R0       ;
06F8 EDF3        DJNZ   R5,BCD03 ;
06FA F6FF        JC     BCDER    ;ERROR IF CARRY
06FC ECE8        DJNZ   R4,BCD02 ;LOOP 16 TIMES
06FE 97          CLR    C        ;NORM RET NO CARRY
06FF 83    BCDER: RET            ;ERROR RETURNS CARRY
0700             ;
0700             ;
0700             ;*********************************************************
0700             ;
0700             ;   *** LIMIT SUBROUTINE ***
0700             ;CHECKS UPPER AND LOWER LIMITS OF TSTVAL
0700             ;AND PROVIDES A CARRY IF @TSTVAL>@LIMMAX
0700             ;OR IF @TSTVAL<@LIMMIN. ALSO, IF
0700             ;@TSTVAL<@LIMMIN THE ACC IS SET TO 01H,
0700             ;IF @TSTVAL>@LIMMIN, ACC IS SET TO 02H.
0700             ;IF LIMIT IS OK THE ACC IS SET TO 00H.
0700 D44C  LIMIT: CALL  CLEAR    ;
0702 B82A        MOV    R0,#TSTVAL
0704 B920        MOV    R1,#20H
```

```
0706 D457              CALL    MOVE2    ;
0708 B828              MOV     R0,#LIMMIN
070A B924              MOV     R1,#24H  ;
070C D457              CALL    MOVE2    ;

070E D408              CALL    SAVREG   ;DO SUBBIN BUT AVOID EXTRA NEST LEVEL
0710 97                CLR     C
0711 D415              CALL    SBIN1    ;
0713 D42A              CALL    GETREG   ;
0715 E61A              JNC     LIMIT1   ;
0717 2301              MOV     A,#01H   ; "LESS THAN" LIMIT INDICATOR
0719 83                RET              ;RETURN WITH CARRY AND ERROR
071A B82A     LIMIT1:  MOV     R0,#TSTVAL
071C B924              MOV     R1,#24H  ;
071E D457              CALL    MOVE2    ;
0720 B82C              MOV     R0,#LIMMAX
0722 B920              MOV     R1,#20H  ;
0724 D457              CALL    MOVE2    ;
0726 D408              CALL    SAVREG   ;DO ANOTHER SUBBIN AS ABOVE
0728 97                CLR     C        ;
0729 D415              CALL    SBIN1    ;
072B D42A              CALL    GETREG   ;
072D E632              JNC     LIMIT2   ;
072F 2302              MOV     A,#02H   ; "GREATER THAN" LIMIT INDICATOR
0731 83                RET              ;RETURN WITH CARRY AND ERROR
0732 2300     LIMIT2:  MOV     A,#00H   ;NO ERROR. NO CARRY, ACC SET TO ZERO
0734 83                RET              ;AND RETURN.
0735                                    ;
0735                   ;************************************************
0735                                    ;BEEP SUBROUTINE
0735                                    ;DISABLES DISPLAY INTERRUPTS OUTPUTTING
0735                                    ;A 7.769KHZ TONE FOR 250 MS.
0735                                    ;USES A,R0-R4
000A         BPFREQ    EQU     10       ;BPFREQ=1/(10US*FREQ) - 3.5
0008         BPTIME    EQU     08       ;BPTIME=(FREQ*ONTIME)/128
0002         BPON      EQU     00000010B    ;USED TO SET BIT 1 WITH OR FN
00FD         BPOFF     EQU     11111101B    ;USED TO RESET BIT 1, AND FN.
0735                                    ;
0735 35      BEEP:     DIS     TCNTI    ;DISABLE INTERRUPTS
0736 B83D              MOV     R0,#3DH  ;POINT TO DISPLAY BUFFER
0738 BA0A              MOV     R2,#BPFREQ   ;USED IN FREQUENCY DELAY LOOP
073A BB80              MOV     R3,#128      ;USED IN ONTIME LOOP
073C BC08              MOV     R4,#BPTIME   ;USED IN ONTIME LOOP
073E F0                MOV     A,@R0    ;GET CURRENT DISPLAY DATA
073F 4302    BPLOOP:   ORL     A,#BPON  ;NOW WE'LL TOGGLE THE SPEAKER BIT
0741 39                OUTL    P1,A     ;ON OFF FOR 250 MS AT THE DESIRED FREQ
0742 F455              CALL    BPDLY    ;
0744 00                NOP              ;
0745 00                NOP              ;
0746 53FD              ANL     A,#BPOFF ;
0748 39                OUTL    P1,A     ;
0749 F455              CALL    BPDLY    ;
074B EB3F              DJNZ    R3,BPLOOP
074D BB80              MOV     R3,#128  ;
074F EC3F              DJNZ    R4,BPLOOP
0751 F0                MOV     A,@R0    ;NOW RESTORE DISPLAY TO ORIGINAL STATUS
0752 39                OUTL    P1,A     ;
0753 25                EN      TCNTI    ;
0754 83                RET              ;THEN RETURN FROM BEEP SUBROUTINE
0755                                    ;
0755 BA0A    BPDLY:    MOV     R2,#BPFREQ
0757 EA57    BPDLY1:   DJNZ    R2,BPDLY1 ;THIS IS THE FREQUENCY DELAY LOOP
0759 83                RET              ;   5US*BPFREQ + 7.5US
075A                   ;************************************************
075A                                    ;UTILIZE SAVSTK AND GETSTK ONLY IN INT
```

```
075A                              ;ROUTINES OR SAVE PSW (SELECTS RBO ON
075A                              ;RETURN)
075A D5      SAVSTK: SEL   RB1    ;
075B AE              MOV   R6,A   ;SAVE ACC
075C B800            MOV   R0,#OOH ;
075E B970            MOV   R1,#70H ;INTO LOC 70-76H
0760 BA07            MOV   R2,#7H ;
0762 F0      SAVST1: MOV   A,@R0  ;GET RBO REG
0763 A1              MOV   @R1,A  ;SAVE IN 70-76
0764 18              INC   R0     ;
0765 19              INC   R1     ;
0766 EA62            DJNZ  R2,SAVST1
0768 FE              MOV   A,R6   ;NOW SAVE ACCUM IN 77
0769 A1              MOV   @R1,A  ;
076A C5              SEL   RBO    ;
076B 83              RET          ;DONE
076C                              ;
076C D5      GETSTK: SEL   RB1    ;
076D B870            MOV   R0,#70H ;
076F B900            MOV   R1,#OOH ;
0771 BA07            MOV   R2,#07H ;
0773 F0      GETST1: MOV   A,@R0  ;GET SAVED VALUE
0774 A1              MOV   @R1,A  ;TO R0-R7
0775 18              INC   R0     ;
0776 19              INC   R1     ;
0777 EA73            DJNZ  R2,GETST1
0779 F0              MOV   A,@R0  ;GET ACCUM
077A C5              SEL   RBO    ;
077B 83              RET          ;DONE
;------------------------------------------------------------
```

I claim:

1. A patient temperature and heartbeat rate monitoring system comprising a plurality of transmitters one for each patient to be monitored, and a receiver,
wherein each transmitter is comprised of sensor means for sensing patient temperature and heartbeat rate and for providing an actual temperature input which has a voltage level proportional to actual patient temperature, a reference temperature input which has a voltage level proportional to a predetermined reference temperatre, and a heartbeat rate input which has a frequency corresponding to heartbeat rate, low pass filter means coupled to said sensor means and receiving said heartbeat rate input for isolating an electrical heartbeat signal having a frequency equal to heartbeat rate, phase lock loop means for receiving said heartbeat signal and for providing a harmonic heartrate signal at a phase controlled frequency which is an upper harmonic of said heartbeat signal, multiplexing means coupled to receive said actual temperature input and said reference temperature input from said sensor means and coupled to receive said heartrate signal from said phase lock loop means, voltage controlled oscillator means coupled to provide an input and receive an output from said multiplexing means, frequency dividing means connecting to receive an input from said voltage controlled oscillator means through said multiplexing means and to provide an output to said multiplexing means, whereby said actual temperature input and said reference temperature input are provided by said sensor means to said voltage controlled oscillator means through said multiplexing means to produce a voltage controlled output signal of frequency proportional to voltage level, and said voltage controlled output signal is provided as an input to said frequency dividing means in sequence with said heartrate signal through said multiplexing means, and said frequency dividing means produces clock and data signals to said multiplexing means of frequency proportional to and stepped down from that of the existing input to said frequency dividing means to sequentially gate each of said voltage level inputs through said multiplexing means to said voltage controlled oscillator means, and said clock and data signals are sequentially at a frequency proportional to voltage level of said reference temperature input, voltage level of said actual temperature input and frequency of said heartbeat rate input, and modulating means for transforming said clock and data signals of said dividing means into radio frequency signals,
and wherein said receiver is comprised of demodulating means for sensing said radio frequency signals and for reproducing said clock and data signals, and signal processing means for producing a visual display from said reproduced clock and data signals.

2. A patient temperture and heartbeat rate monitoring system comprising a plurality of transmitters, one associated with each patient to be monitored, and a receiver,
each transmitter comprising:
reference temperature resistor means,
a first electrode for securement to the skin of a patient to be monitored in electrical contact therewith,
a thermistor mounted on said first electrode adapted to be in thermal contact with the skin of said patient,
a second electrode for securement to the skin of said patient,
means for applying voltage to said reference temperature resistor means to produce a reference temperature input which is at a voltage level proportional to the value of said reference temperature resistor means and for applying voltage and to said thermistor to produce an actual temperature input which is at a voltage level proportional to the temperature of said patient, means connected to said first and second electrodes for monitoring voltage differential therebetween and for producing heartbeat signals at a frequency proportional to the heartbeat rate of said patient as a heartbeat rate input, transducer means comprised of low pass filter means coupled to said means for monitoring voltage differential between said first and second electrodes for isolating an electrical heartbeat signal having a frequency equal to heartbeat rate, phase lock loop means for receiving said heartbeat signal and for providing a harmonic heartrate signal at a phase controlled frequency which is an upper harmonic of said heatbeat signal, multiplexing means, voltage controlled oscillator means coupled to provide an input to and receive an output from said multiplexing means, and frequencey dividing means connected to receive an input from said voltage controlled oscillator means through said multiplexing means and to provide an output to said multiplexing means, whereby said voltage levels of said reference temperature input and said actual temperature input are provided by said reference temperature resistor means and said thermistor to said voltage controlled oscillator means through said multiplexing means to produce a voltage controlled output signal of frequency proportional to voltage level, and said voltage controlled output signal is provided as an input to said frequency dividing means through said multiplexing means, and said heartrate signal is also provided as an input to said frequency dividing means through said multiplexing means, and said frequency dividing means produces a clock output to said multiplexing means for frequency proportional to and stepped down from that of the existing input to said frequency dividing means to sequentially gate said reference temperature input and said actual temperature input through said multiplexing means to said voltage controlled oscillator means, and said clock output is also connected to said multiplexing means to sequentially gate said output signal and said heartrate signal through said multiplexing means to said frequency dividing means, and modulating means for receiving said clock output from said frequency dividing means to modulate a carrier signal to generate radio signals corresponding to said reference temperature, actual temperature and patient heartbeat rate, said receiver comprising:

demodulating means for demodulating said radio signals to produce data signals corresponding to said reference temperature, actual temperature and heartbeat rate, and signal processing means for converting said data signals to indicia indicative of patient temperature and heartbeat rate.

3. A patient temperature and heartbeat rate monitoring system comprising a plurality of transmitters, one associated with each patient to be monitored, and a receiver, each transmitter comprising:
reference temperature resistor means, a first electrode for securement to the skin of a patient to be monitored in electrical contact therewith, a thermistor mounted on said first electrode in thermal contact with the skin of said patient, a second electrode for securement to the skin of said patient, means for applying voltage to said reference temperature resistor means to produce a reference temperature input which is at a voltage level proportional to the value of said reference temperature resistor means and for applying voltage to said thermistor to produce an actual temperature input which is at a voltage level proportional to the temperature of said patient, means connected to said first and second electrodes for monitoring voltage differential therebetween and for producing heartbeat signals at a frequency proportional to the heartbeat rate of said patient as a heartbeat rate input, transducer means comprising low pass filter means coupled to said means for monitoring voltage differential between said first and second electrodes for isolating an electrical heartbeat signal having a frequency equal to heartbeat rate, phase lock loop means for receiving said heartbeat signal and for providing a harmonic heartrate signal at a phase controlled frequency which is an upper harmonic of said heartbeat signal, multiplexing means, voltage controlled oscillator means coupled to provide an input to and receive an output from said multiplexing means, and frequency dividing means connected to receive an input from said voltage controlled oscillator means through said multiplexing means and to provide an output to said multiplexing means, whereby said voltage levels of said reference temperature input and said actual temperature input are provided by said reference temperature resistor means and said thermistor to said voltage controlled oscillator means through said multiplexing means to produce a voltage controlled output signal of frequency proportional to voltage level, and said voltage controlled output signal is provided as an input to said frequency dividing means through said multiplexing means, and said heartrate signal is also provided as an input to said frequency dividing means through said multiplexing means, and said frequency dividing means produces a clock output to said multiplexing means of frequency proportional to and stepped down from that of the existing input to said frequency dividing means to sequentially gate said reference temperature input and said actual temperature input through said multiplexing means to said voltage controlled oscillator means, and said clock output is also connected to said multiplexing means to sequentially gate said voltage controlled output signal and said heartrate signal through said multiplexing means to said frequency dividing means and, modulating means for receiving said clock output from said frequency dividing means to modulate a carrier signal to generate radio signals corresponding to said reference temperature actual temperature and patient heartbeat rate, said receiver comprising:

demodulating means for demodulating said radio signals to produce envelope signals corresponding to said reference temperature, actual temperature and patient heartbeat rate, and microprocessor means coupled to receive inputs from said demodulating means to convert said envelope signals to numeric data signals indicative of patient temperature and heartbeat rate.

4. A patient temperature and heartbeat rate monitoring system according to claim 3 wherein each of said transmitters is powered by a self contained battery, and said means for producing said actual temperature input and said reference temperature input includes means for generating an electrical transmitter battery level signal proportional to the voltage level of said battery, and said modulating means provides a radio frequency transmitter battery level signal, and said demodulating means provides a transmitter battery envelope signal of duration proportional to said transmitter battery level signal, and said microprocessor means includes means for suppressing said numeric data signals when the duration of said transmitter battery envelope signal is less than a predetermined minimum value.

5. A patient temperature and heartbeat monitoring system according to claim 4 wherein said transmitter includes a normally open magnetically operable switch for activating said means for producing said actual temperature input and said reference temperature input, and said receiver includes a magnet for closing the magnetically operable switch of a transmitter when brought into close proximity thereto.

6. A patient temperature and heartbeat rate monitoring system according to claim 1 wherein each transmitter includes a transmitter battery and a means for generating a data signal input of a voltage proportional to said transmitter battery voltage as an input to said multiplexing means and to said voltage controlled oscillator means in sequence with said reference temperature input and said actual temperature input.

7. A patient temperature and heartrate monitoring system according to claim 1 wherein said receiver includes display means coupled to said signal processing means for producing a visible numeric display, said signal processing means in said receiver includes means for separately converting the duration of said clock and data signals to numerical values of patient temperature and patient heartrate and for providing said numerical values to said display means, and said receiver includes manually actuable mode selection means for controlling said display means to selectively and alternatively display numerical values of patient temperature and patient heartrate.

8. A patient temperature and heartrate monitoring system according to claim 7 wherein said receiver also includes means for generating test signals of predetermined duration coupled to said signal processing means, and manually actuable test selection means for directing said test signals to said signal processing means and for concurrently suppressing said reproduced clock and data signals.

9. A patient temperature and pulse rate monitoring system according to claim 2 wherein said means for applying voltage includes separate conductors each connected to one side of each of said reference temperature resistor means and said thermistor, and a ground conductor connected to the opposite sides of said reference temperature resistor means and said thermistor and to an electrical ground.

10. A patient temperature and heartrate monitoring system according to claim 9 wherein said ground conductor is electrically connected to said first electrode and said means for monitoring voltage differential between said first and second electrodes includes said ground conductor and a heartbeat signal conductor electrically isolated from said first electrode and electrically connected to said second electrode.

11. A patient temperature and heartrate monitoring system according to claim 10 wherein said conductor connected to said one side of said thermistor and said ground conductor are comprised of a twisted pair of insulated wires and said heartbeat signal conductor is comprised of an insulated, braided shield surrounding said twisted pair of wires.

12. A patient temperature and heartrate monitoring system according to claim 10 wherein said first and second electrodes both include patient contact surfaces covered with electrode gel.

* * * * *